(12) United States Patent
Rothschild

(10) Patent No.: US 11,024,339 B2
(45) Date of Patent: Jun. 1, 2021

(54) SYSTEM AND METHOD FOR TESTING FOR COVID-19

(71) Applicant: Richard A Rothschild, London (GB)

(72) Inventor: Richard A Rothschild, London (GB)

(*) Notice: Subject to any disclaimer, the term of this patent is extended or adjusted under 35 U.S.C. 154(b) by 0 days.

(21) Appl. No.: 16/876,114

(22) Filed: May 17, 2020

(65) Prior Publication Data

US 2020/0279585 A1  Sep. 3, 2020

Related U.S. Application Data

(63) Continuation-in-part of application No. 16/704,844, filed on Dec. 5, 2019, which is a continuation of application No. 16/273,141, filed on Feb. 11, 2019, now Pat. No. 10,522,188, which is a continuation of application No. 15/495,485, filed on Apr. 24, 2017, now Pat. No. 10,242,713, which is a continuation of application No. 15/293,211, filed on Oct. 13, 2016, now abandoned.

(60) Provisional application No. 62/240,783, filed on Oct. 13, 2015.

(51) Int. Cl.
| | |
|---|---|
| *G11B 27/10* | (2006.01) |
| *G11B 27/031* | (2006.01) |
| *G06K 9/00* | (2006.01) |
| *H04N 9/82* | (2006.01) |
| *G16H 40/63* | (2018.01) |
| *H04N 5/76* | (2006.01) |

(52) U.S. Cl.
CPC .......... *G11B 27/10* (2013.01); *G06K 9/00892* (2013.01); *G11B 27/031* (2013.01); *G11B 27/102* (2013.01); *G16H 40/63* (2018.01); *H04N 5/76* (2013.01); *H04N 9/8205* (2013.01); *G06K 2009/00939* (2013.01)

(58) Field of Classification Search
CPC ... G11B 27/10; G06K 9/00892; H04N 9/8205
See application file for complete search history.

(56) References Cited

U.S. PATENT DOCUMENTS

2015/0366518 A1* 12/2015 Sampson ............. A61B 5/0478
600/301

\* cited by examiner

*Primary Examiner* — Girumsew Wendmagegn
(74) *Attorney, Agent, or Firm* — Fitzsimmons IP Law

(57) ABSTRACT

A method is provided for acquiring and transmitting biometric data (e.g., vital signs) of a user, where the data is analyzed to determine whether the user is suffering from a viral infection, such as COVID-19. The method includes using a pulse oximeter to acquire at least pulse and blood oxygen saturation percentage, which is transmitted wirelessly to a smartphone. To ensure that the data is accurate, an accelerometer within the smartphone is used to measure movement of the smartphone and/or the user. Once accurate data is acquired, it is uploaded to the cloud (or host), where the data is used (alone or together with other vital signs) to determine whether the user is suffering from (or likely to suffer from) a viral infection, such as COVID-19. Depending on the specific requirements, the data, changes thereto, and/or the determination can be used to alert medical staff and take corresponding actions.

17 Claims, 23 Drawing Sheets

400

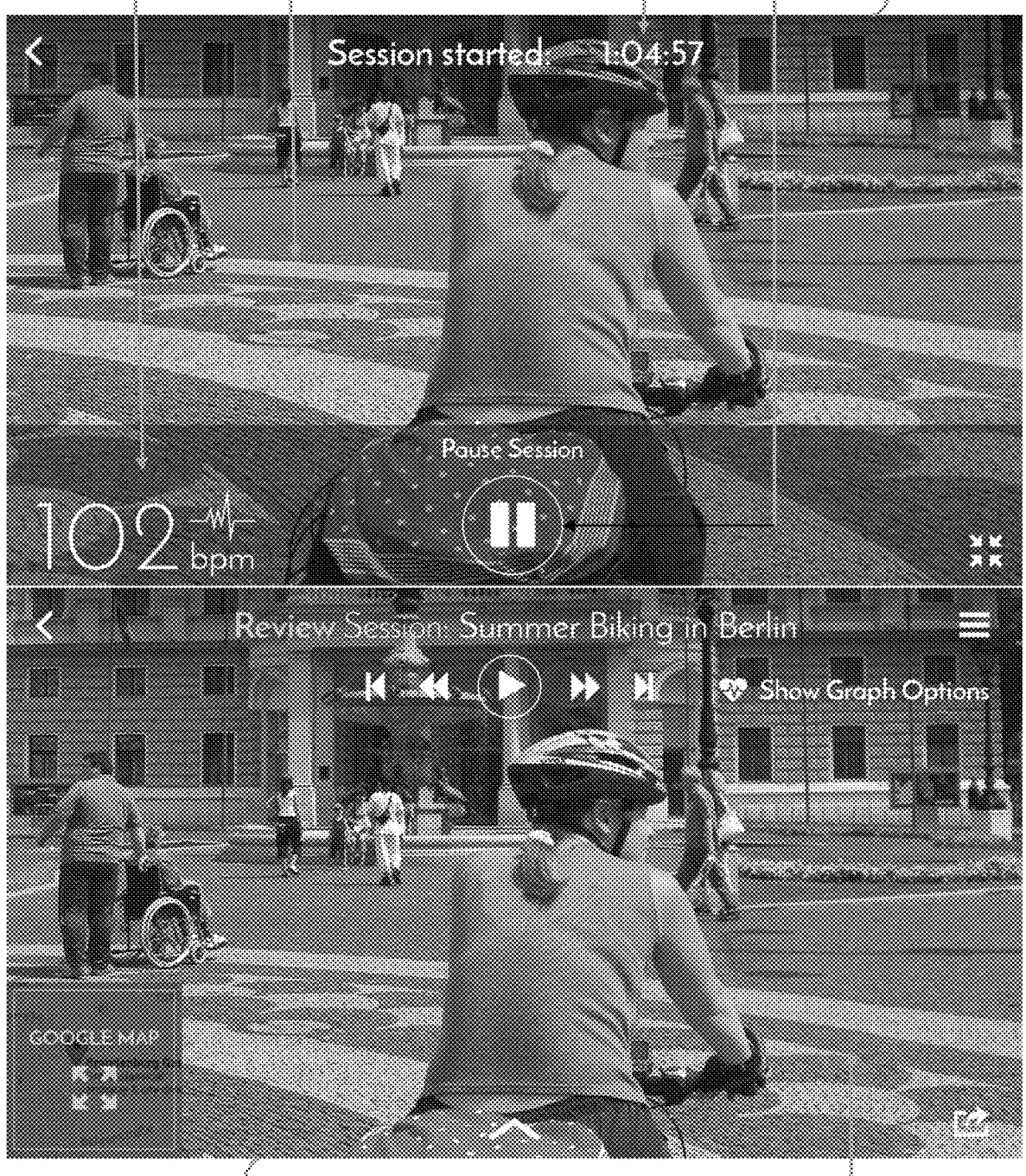

Figure 21
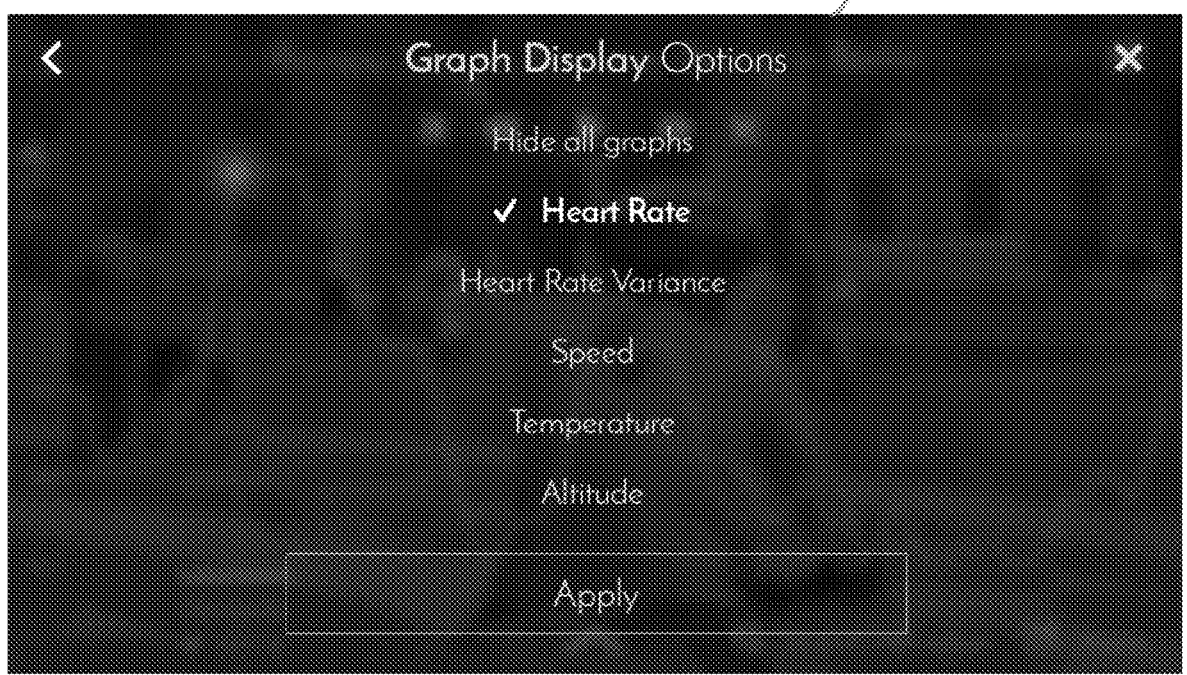
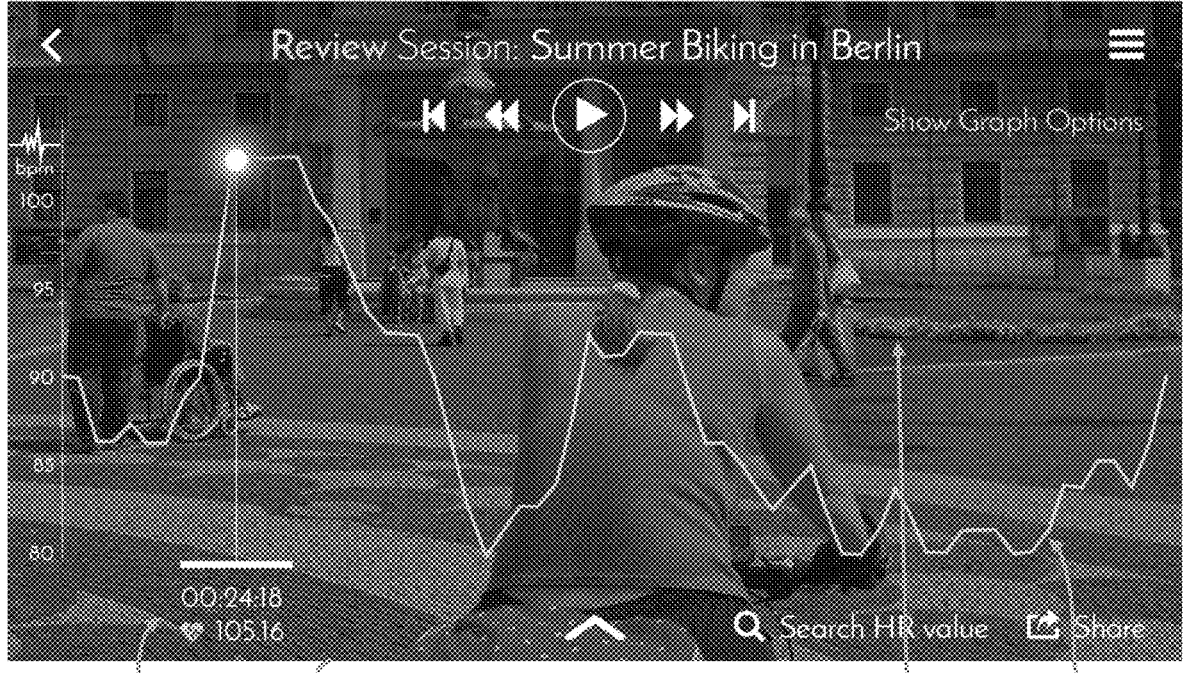
Figure 22

Figure 25
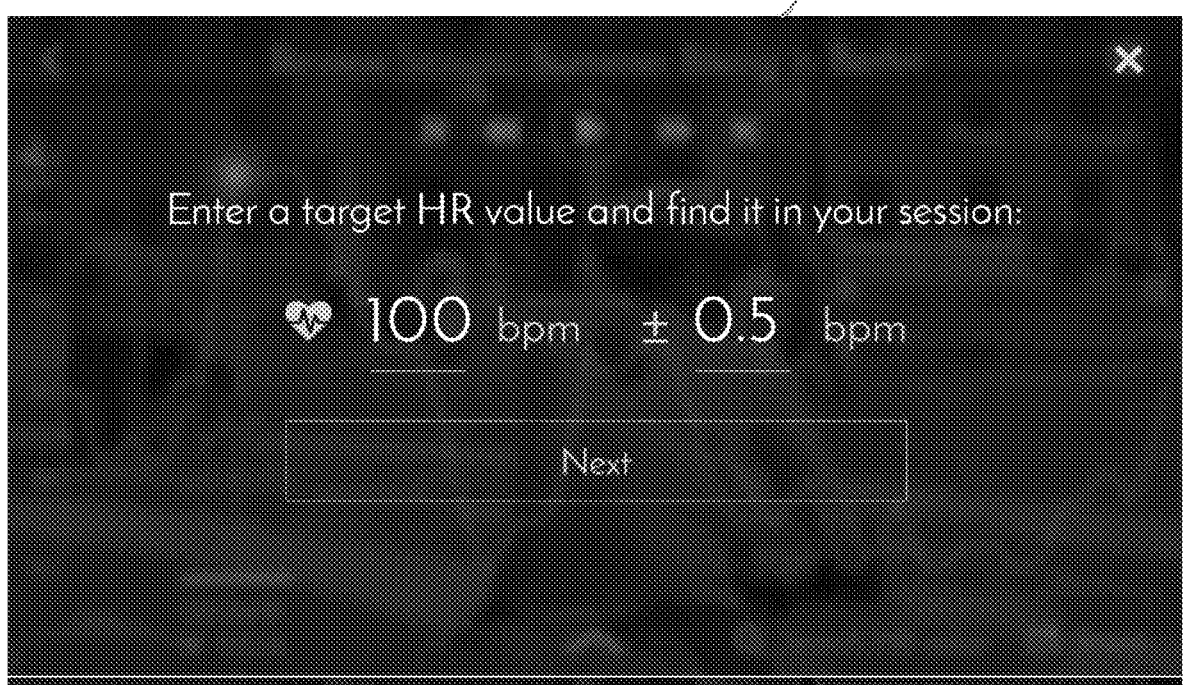
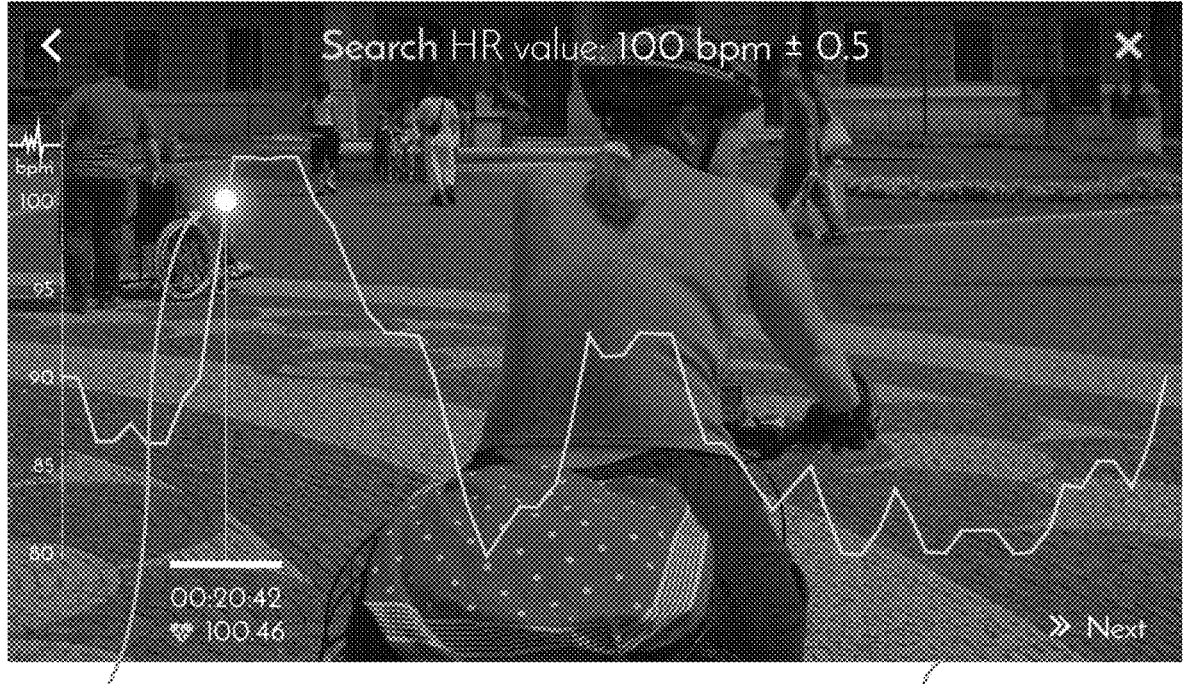
Figure 26

SYSTEM AND METHOD FOR TESTING FOR COVID-19

BACKGROUND OF THE INVENTION

1. Field of the Invention

The present invention relates to diagnosing an individual's health/wellness, and more particularly, to a system and method for using a mobile computing device (e.g., a smartphone) to acquire and provide vital signs, which can then be used to determine (or aid in the determination of) an individual's health/wellness, including whether an individual is suffering from a bacterial and/or viral infection (e.g., COVID-19, etc.) or other respiratory conditions or symptoms. The present invention could be used in conjunction with a telemedicine or "digital health" system to provide a reliable and convenient method for remote collection and observation of a patient's vital signs.

2. Description of Related Art

Recently, devices have been developed that are capable of measuring, sensing, or estimating in a convenient form factor at least one or more metric related to physiological characteristics, commonly referred to as biometric data. For example, devices that resemble watches have been developed which are capable of measuring an individual's heart rate or pulse, and, using that data together with other information (e.g., the individual's age, weight, etc.), to calculate a resultant, such as the total calories burned by the individual in a given day. Similar devices have been developed for measuring, sensing, or estimating other kinds of metrics, such as blood pressure, blood oxygenation levels, breathing patterns, breath composition, sleep patterns, and blood-alcohol level, to name a few. These devices are generically referred to as biometric devices or biosensor metrics devices.

The types of biometric devices continue to grow, as do the ways in which both the core biometric data and the data that can additionally be derived or further extrapolated from that biometric data. For example, heart rate data is typically used to give an individual information on their pulse and calories burned, whereas HRV or heart rate variability is sometimes also increasingly being used as a determinant of an individual's stress levels. The data measured from oximeters (perfusion index, oxygen saturation level and pulse) can additionally be used to derive algorithmically the individual's respiratory rate or RR. By way of another example, blood-alcohol data is typically used to give an individual information on their blood-alcohol level, and hence to inform the individual on whether or not they can safely or legally operate a motor vehicle.

By way other examples, an individual's breathing pattern (measurable for example either by loudness level in decibels, or by variations in decibel level over a time interval), or measurable changes over a short space of time in levels of oxygen saturation in their blood caused by a stopped or snore breathing event (SBE), or by the total number of SBEs occurring during sleep, may be monitored by a doctor, nurse, or medical technician to help determine whether the individual suffers from sleep apnea. Similarly, an individual's vital signs (e.g., pulse, breathing rate, oxygen saturation levels, etc.) may be monitored (e.g., by a doctor, etc.) to determine the individual's health and/or wellness in relation to certain medical conditions or symptoms. Such information can also be used to determine whether a person is suffering from a bacterial and/or viral infection, such as coronavirus, or COVID-19.

With that being said, it would be beneficial if biometric data could be acquired and provided to a medical facility or the like without requiring human contact between the patient and the monitoring staff (i.e., remotely) for reasons including convenience, cost and diminished risk of infection or cross infection. The biometric data would also be more informative or dynamic if it could be combined with other data (e.g., video data, etc.), provided (e.g., wirelessly, over a network, etc.) to a remote device, and/or searchable (e.g., allowing certain conditions, such as an elevated heart rate or hypoxia, to be quickly identified) and/or cross-searchable (e.g., using biometric data to identify a video section illustrating a specific characteristic, or vice-versa). Thus, a need exists for an efficient system and method capable of achieving at least some, or indeed all, of the foregoing advantages, and capable also of merging the data generated in either automatic or manual form by the various devices, which are often using operating systems or technologies (e.g., hardware platforms, protocols, data types, etc.) that are incompatible with one another.

In certain embodiments of the present invention, remote collection of biometric data (e.g., vital signs, etc.) could be used to enable or enhance telemedicine procedures and carry out diagnostics. This could be an extremely valuable tool, especially during the current COVID-19 pandemic, in that it would reduce risk of infectious exposure (both to patient and medical staff) and provide a reliable, convenient, and cost effective method for remote collection and frequent observation of a patient's vital signs. The system could be utilized both pre- and post-hospitalization or treatment.

In a pre-hospitalization context, where individuals are experiencing symptoms, or have already been in contact with medical services and not yet been (or needed to be) hospitalized but are nevertheless in need of regular observation for any change in their condition, this would allow for consistent and timely monitoring of the patients' vital signs. Once the vital signs are recorded, the data can be uploaded automatically to the medical services. In a post-hospitalization utilization, if the patient is considered well enough to continue recovery and convalescence at home, it could allow for an earlier discharge from hospital (freeing up hospital beds), while still having the patient's condition monitored without having to rely on medical staff physically collecting their vital signs. In both cases, vital signs could be uploaded to the cloud, providing medical services with a digital record of its evolution, as well as integration into the patient record keeping system or electronic health record (EHR).

Such a system would be beneficial, especially in light of the current COVID-19 pandemic, by: (1) reducing physical contact between patient and medical facility or staff, thereby minimizing the risk of infection in either direction; (2) increasing patient convenience, as well as the capability for quicker medical response if necessary; (3) reducing human resources, and therefore costs; (4) making more effective use of medical staff, thereby allowing them to spend more time on patient treatment; (5) allowing for more regular recording of vital signs with a digital, searchable record of the evolution of the same; (6) providing anonymized but richer, data to derive potentially significant trends both for the individual and the COVID-19 symptomatic population taken as a whole, extrapolated from demographics and progress of illness or recovery; (7) better utilizing critical care facilities and planning/scheduling of in-hospital resource availability; (8) lowering cost of diagnostic equipment and accompanying software infrastructure, in comparison to the current use of medical staff to fulfill the function of recording vital signs; and (8) providing for more frequent and timely recording of vital sign, since there is no restriction linked to the availability or cost of medical staff to take the measurements.

In other embodiments of the present invention, the system and/or method is configured to receive, manage, and filter the quantity of information on a timely and cost-effective basis, and could also be of further value through the accurate measurement, visualization (e.g., synchronized visualization, etc.), and rapid notification of data points which are outside (or within) a defined or predefined range.

Such a system and/or method could be used by an individual (e.g., athlete, etc.) or their trainer, coach, etc., to visualize the individual during the performance of an athletic event (e.g., jogging, biking, weightlifting, playing soccer, etc.) in real-time (live) or afterwards, together with the individual's concurrently measured biometric data (e.g., heart rate, etc.), and/or concurrently gathered "self-realization data," or subject-generated experiential data, where the individual inputs their own subjective physical or mental states during their exercise, fitness or sports activity/training (e.g., feeling the onset of an adrenaline "rush" or endorphins in the system, feeling tired, "getting a second wind," etc.). This would allow a person (e.g., the individual, the individual's trainer, a third party, etc.) to monitor/observe physiological and/or subjective psychological characteristics of an individual while watching or reviewing the individual in the performance of an athletic event, or other physical activity. Such inputting of the self-realization data, ca be achieved by various methods, including automatically, time-stamped-in-the-system voice notes, short-form or abbreviation key commands on a smart phone, smart watch, enabled fitness band, or any other system-linked input method which is convenient for the individual to utilize so as not to impede (or as little as possible) the flow and practice by the individual of the activity in progress.

Such a system and/or method would also facilitate, for example, remote observation and diagnosis in telemedicine applications, where there is a need for the medical staff, or monitoring party or parent, to have clear and rapid confirmation of the identity of the patient or infant, as well as their visible physical condition, together with their concurrently generated biometric and/or self-realization data.

Furthermore, the system and/or method should also provide the subject, or monitoring party, with a way of using video indexing to efficiently and intuitively benchmark, map and evaluate the subject's data, both against the subject's own biometric history and/or against other subjects' data samples, or demographic comparables, independently of whichever operating platforms or applications have been used to generate the biometric and video information. By being able to filter/search for particular events (e.g., biometric events, self-realization events, physical events, etc.), the acquired data can be reduced down or edited (e.g., to create a "highlight reel," etc.) while maintaining synchronization between individual video segments and measured and/or gathered data (e.g., biometric data, self-realization data, GPS data, etc.). Such comprehensive indexing of the events, and with it the ability to perform structured aggregation of the related data (video and other) with (or without) data from other individuals or other relevant sources, can also be utilized to provide richer levels of information using methods of "Big Data" analysis and "Machine Learning," and adding artificial intelligence ("AI") for the implementation of recommendations and calls to action.

SUMMARY OF THE INVENTION

The present invention provides a system and method for acquiring, processing, transmitting, comparing and/or displaying biometric data, or a resultant thereof (e.g., assisting in determining whether the user suffers from a particular ailment (e.g., COVID-19)), either alone or together (e.g., in synchronization) with other data (e.g., video data, etc.). Preferred embodiments of the present invention operate in accordance with a computing device (e.g., a smart phone, etc.) in communication with at least one external device (e.g., a biometric device for acquiring biometric data including vital signs, a video device for acquiring video data, etc.). In a first embodiment of the present invention, video data, which may include audio data, and non-video data, such as biometric data, are stored separately on the computing device and linked to other data, which allows searching and synchronization of the video and non-video data.

In one embodiment of the present invention, an application (e.g., running on the computing device, etc.) includes a plurality of modules for performing a plurality of functions. For example, the application may include a video capture module for receiving video data from an internal and/or external camera, and a biometric capture module for receiving biometric data from an internal and/or external biometric device. The client platform may also include a user interface module, allowing a user to interact with the platform, a video editing module for editing video data, a file handling module for managing data, a database and sync module for replicating data, an algorithm module for processing received data, a sharing module for sharing and/or storing data, and a central login and ID module for interfacing with third party social media websites, such as Facebook™.

These modules can be used, for example, to start a new session, receive video data for the session (i.e., via the video capture module) and receive biometric data for the session (i.e., via the biometric capture module). This data can be stored in local storage, in a local database, and/or on a remote storage device (e.g., in the company cloud or a third-party cloud service, such as Dropbox™, etc.). In a preferred embodiment, the data is stored so that it is linked to information that (i) identifies the session and (ii) enables synchronization.

For example, video data is preferably linked to at least a start time (e.g., a start time of the session) and an identifier. The identifier may be a single number uniquely identifying the session, or a plurality of numbers (e.g., a plurality of global or universal unique identifiers (GUIDs/UUIDs)), where a first number uniquely identifying the session and a second number uniquely identifies an activity within the session, allowing a session to include a plurality of activities. The identifier may also include a session name and/or a session description. Other information about the video data (e.g., video length, video source, etc.) (i.e., "video metadata") can also be stored and linked to the video data. Biometric data is preferably linked to at least the start time (e.g., the same start time linked to the video data), the identifier (e.g., the same identifier linked to the video data), and a sample rate, which identifies the rate at which biometric data is received and/or stored.

Once the video and biometric data is stored and linked, algorithms can be used to display the data together. For example, if biometric data is stored at a sample rate of 30 samples per minute (spm), algorithms can be used to display a first biometric value (e.g., below the video data, superimposed over the video data, etc.) at the start of the video clip, a second biometric value two seconds later (two seconds into the video clip), a third biometric value two seconds later (four seconds into the video clip), etc. In alternate embodiments of the present invention, non-video data (e.g., biometric data, self-realization data, etc.) can be stored with a plurality of time-stamps (e.g., individual stamps or offsets for each stored value, or individual sample rates for each data type), which can be used together with the start time to synchronize non-video data to video data.

In one embodiment of the present invention, the biometric device may include a sensor for sensing biometric data, a display for interfacing with the user and displaying various information (e.g., biometric data, set-up data, operation data, such as start, stop, and pause, etc.), a memory for storing the sensed biometric data, a transceiver for communicating with the exemplary computing device, and a processor for operating and/or driving the transceiver, memory, sensor, and display. The exemplary computing device includes a transceiver(1) for receiving biometric data from the exemplary biometric device, a memory for storing the biometric data, a display for interfacing with the user and displaying various information (e.g., biometric data, set-up data, operation data, such as start, stop, and pause, input in-session comments or add voice notes, etc.), a keyboard (or other user input) for receiving user input data, a transceiver(2) for providing the biometric data to the host computing device via the Internet, and a processor for operating and/or driving the transceiver (1), transceiver(2), keyboard, display, and memory.

The keyboard (or other input device) in the computing device, or alternatively the keyboard (or other input device) in the biometric device, may be used to enter self-realization data, or data on how the user is feeling at a particular time. For example, if the user is feeling tired, the user may enter the "T" on the keyboard. If the user is feeling their endorphins kick in, the user may enter the "E" on the keyboard. And if the user is getting their second wind, the user may enter the "S" on the keyboard. Alternatively, to further facilitate operation during the exercise, or sporting activity, short-code key buttons such as "T," "E," and "S" can be preassigned, like speed-dial telephone numbers for frequently called contacts on a smart phone, etc., which can be selected manually or using voice recognition. This data (e.g., the entry or its representation) is then stored and linked to either a sample rate (like biometric data) or time-stamp data, which may be a time or an offset to the start time that each button was pressed. This would allow the self-realization data to be synchronized to the video data. It would also allow the self-realization data, like biometric data, to be searched or filtered (e.g., in order to find video corresponding to a particular event, such as when the user started to feel tired, etc.).

In an alternate embodiment of the present invention, the computing device (e.g., a smart phone, etc.) is also in communication with a host computing device via a wide area network ("WAN"), such as the Internet. This embodiment allows the computing device to download the application from the host computing device, offload at least some of the above-identified functions to the host computing device, and store data on the host computing device (e.g., allowing video data, alone or synchronized to non-video data, such as biometric data and self-realization data, to be viewed by another networked device). For example, the software operating on the computing device (e.g., the application, program, etc.) may allow the user to play the video and/or audio data, but not to synchronize the video and/or audio data to the biometric data. This may be because the host computing device is used to store data critical to synchronization (time-stamp index, metadata, biometric data, sample rate, etc.) and/or software operating on the host computing device is necessary for synchronization. By way of another example, the software operating on the computing device may allow the user to play the video and/or audio data, either alone or synchronized with the biometric data, but may not allow the computing device (or may limit the computing device's ability) to search or otherwise extrapolate from, or process the biometric data to identify relevant portions (e.g., which may be used to create a "highlight reel" of the synchronized video/audio/biometric data) or to rank the biometric and/or video data. This may be because the host computing device is used to store data critical to search and/or to rank the biometric data (biometric data, biometric metadata, etc.), and/or software necessary for searching (or performing advanced searching of) and/or ranking (or performing advanced ranking of) the biometric data.

In one embodiment, as discussed above, the present invention can also be used to address concerns with the current COVID-19 (coronavirus) pandemic. For example, the present invention may be used to provide telemedicine services, allowing diagnostic checks to be conducted in a safe, reliable, and convenient manner, and to do so more efficiently and with reduced risk of infection exposure both for patients and medical staff.

In this embodiment, a communication device, such as a smartphone, other mobile connected device or fixed or mobile IoT device, would communicate (e.g., wirelessly or physically connected via a port on the device) with a pulse oximeter attached to or otherwise in contact with a patient. The pulse oximeter would provide the communication device, such as a smartphone, with pulse oximeter data over a given period of time (e.g., ten seconds, etc.), which may include at least pulse measurement and blood oxygen saturation percentage (or level). The data could then be uploaded to the cloud (or host) and used to assist in determining whether the patient is suffering from an illness, such as COVID-19, or, if the patient has already been diagnosed as such and has had treatment and is subsequently convalescing, to assist in determining whether the patient is now recovering from illness, or not. Depending on the specific requirements of the medical service (hospital, doctor, medical insurance company, etc.), the incoming data can be used to alert the medical staff of any change in vital signs (or determination) requiring an action to be taken.

While different biometrics (e.g., temperature, etc.) can be used in helping to determine whether a patient is suffering from COVID-19, pulse oximeter data also is particularly relevant as the virus is very often accompanied by respiratory insufficiency or reduced pulmonary function, and can therefore be detected by analyzing the patient's blood oxygen saturation percentage (or level) as well as the other data from the oximeter including perfusion index and pulse rate. However, pulse oximeter accuracy is dependent on the patient remaining still, as well as the oximeter, in relation to the patient, also not being moved since movement of the oximeter, attached in one or other form to the patient, often results in the generation of incorrect data.

Thus, it may be necessary for the present invention to determine whether the patient is moving (or not remaining sufficiently still) during the time that the pulse oximeter data is being acquired. In one embodiment, this is accomplished using the accelerometer within the smartphone, since at the time of acquisition of the data, the oximeter is connected typically by Bluetooth or other available data transport protocol to the communication device. An accelerometer is an electromechanical device used to measure acceleration forces, or a change in velocity. By using the accelerometer in the smartphone, the system can ensure that the patient is not moving (or moving very little) while pulse oximeter data (or other vital signs) are being acquired.

With respect to embodiments of the present invention involving video, the video data, which may also include audio data, may start at a time "T" and continue for a duration of "n." The video data is preferably stored in memory (locally and/or remotely) and linked to other data, such as an identifier, start time, and duration. Such data ties the video data to at least a particular session, a particular start time, and identifies the duration of the video included therein. In one embodiment of the present invention, each session can include different activities. For example, a trip to Berlin on a particular day (session) may involve a bike ride through the city (first activity) and a walk through a park (second activity). Thus, the identifier may include both a session identifier, uniquely identifying the session via a globally unique identifier (GUID), and an activity identifier, uniquely identifying the activity via a globally unique identifier (GUID), where the session/activity relationship is that of a parent/child.

In one embodiment of the present invention, the biometric data is stored in memory and linked to the identifier and a sample rate "m." This allows the biometric data to be linked to video data upon playback. For example, if identifier is one, start time is 1:00 PM, video duration is one minute, and the sample rate is 30 spm, then the playing of the video at 2:00 PM would result in the first biometric value to be displayed (e.g., below the video, over the video, etc.) at 2:00 PM, the second biometric value to be displayed (e.g., below the video, over the video, etc.) two seconds later, and so on until the video ends at 2:01 PM. While self-realization data can be stored like biometric data (e.g., linked to a sample rate), if such data is only received periodically, it may be more advantageous to store this data linked to the identifier and a time-stamp, where "m" is either the time that the self-realization data was received or an offset between this time and the start time (e.g., ten minutes and four seconds after the start time, etc.). By storing video and non-video data separately from one another, data can be easily search and synchronized.

With respect to linking data to an identifier, which may be linked to other data (e.g., start time, sample rate, etc.), if the data is received in real-time, the data can be linked to the identifier(s) for the current session (and/or activity). However, when data is received after the fact (e.g., after a session has ended), there are several ways in which the data can be linked to a particular session and/or activity (or identifier(s) associated therewith). The data can be manually linked (e.g., by the user) or automatically linked via the application. With respect to the latter, this can be accomplished, for example, by comparing the duration of the received data (e.g., the video length) with the duration of the session and/or activity, by assuming that the received data is related to the most recent session and/or activity, or by analyzing data included within the received data. For example, in one embodiment, data included with the received data (e.g., metadata) may identify a time and/or location associated with the data, which can then be used to link the received data to the session and/or activity. In another embodiment, the computing device could display data (e.g., a barcode, such as a QR code, etc.) that identifies the session and/or activity. An external video recorder could record the identifying data (as displayed by the computing device) along with (e.g., before, after, or during) the user and/or his/her surroundings. The application could then search the video data for identifying data and use this data to link the video data to a session and/or activity. The identifying portion of the video data could then be deleted by the application if desired.

A more complete understanding of a system and method for using, processing, and displaying biometric data, or a resultant thereof, will be afforded to those skilled in the art, as well as a realization of additional advantages and objects thereof, by a consideration of the following detailed description of the preferred embodiment. Reference will be made to the appended sheets of drawings, which will first be described briefly.

BRIEF DESCRIPTION OF THE DRAWINGS

FIG. 19 depicts an exemplary "session started" screen shot for the application depicted in FIG. 15, showing the video and biometric data received in real-time;

FIG. 20 depicts an exemplary "review session" screen shot for the application depicted in FIG. 15, allowing the user to playback the session at a later time;

FIG. 21 depicts an exemplary "graph display option" screen shot for the application depicted in FIG. 15, allowing the user to select data (e.g., heart rate data, etc.) to be displayed along with the video data;

FIG. 22 depicts an exemplary "review session" screen shot for the application depicted in FIG. 15, where the video data is displayed together (or in synchronization) with the biometric data;

FIG. 25 depicts an exemplary "biometric search" screen shot for the application depicted in FIG. 15, allowing a user to search the biometric data for particular biometric event (e.g., a particular value, a particular range, etc.);

FIG. 26 depicts an exemplary "first result" screen shot for the application depicted in FIG. 15, showing a first result for the biometric event shown in FIG. 25, together with corresponding video;

DETAILED DESCRIPTION OF THE PREFERRED EMBODIMENT

The present invention provides a system and method for acquiring, processing, transmitting, comparing and/or displaying biometric data, or a resultant thereof (e.g., a determination as to whether the user is suffering from an ailment, such as COVID-19), either alone or together (e.g., in synchronization) with other data (e.g., video data, etc.). It should be appreciated that while the invention is described herein in terms of certain biometric data (e.g., heart rate, breathing patterns, blood-alcohol level, etc.), the invention is not so limited, and can be used in conjunction with any biometric and/or physical data, including, but not limited to oxygen levels, $CO_2$ levels, oxygen saturation, blood pressure, blood glucose, lung function, eye pressure, body and ambient conditions (temperature, humidity, light levels, altitude, and barometric pressure), speed (walking speed, running speed), location and distance travelled, breathing rate, heart rate variance (HRV), EKG data, perspiration levels, calories consumed and/or burnt, ketones, waste discharge content and/or levels, hormone levels, blood content, saliva content, audible levels (e.g., snoring, etc.), mood levels and changes, galvanic skin response, brain waves and/or activity or other neurological measurements, sleep patterns, physical characteristics (e.g., height, weight, eye color, hair color, iris data, fingerprints, etc.) or responses (e.g., facial changes, retinal, iris (or pupil) changes, voice (or tone) changes, etc.), or any combination or resultant thereof.

Figure 1:
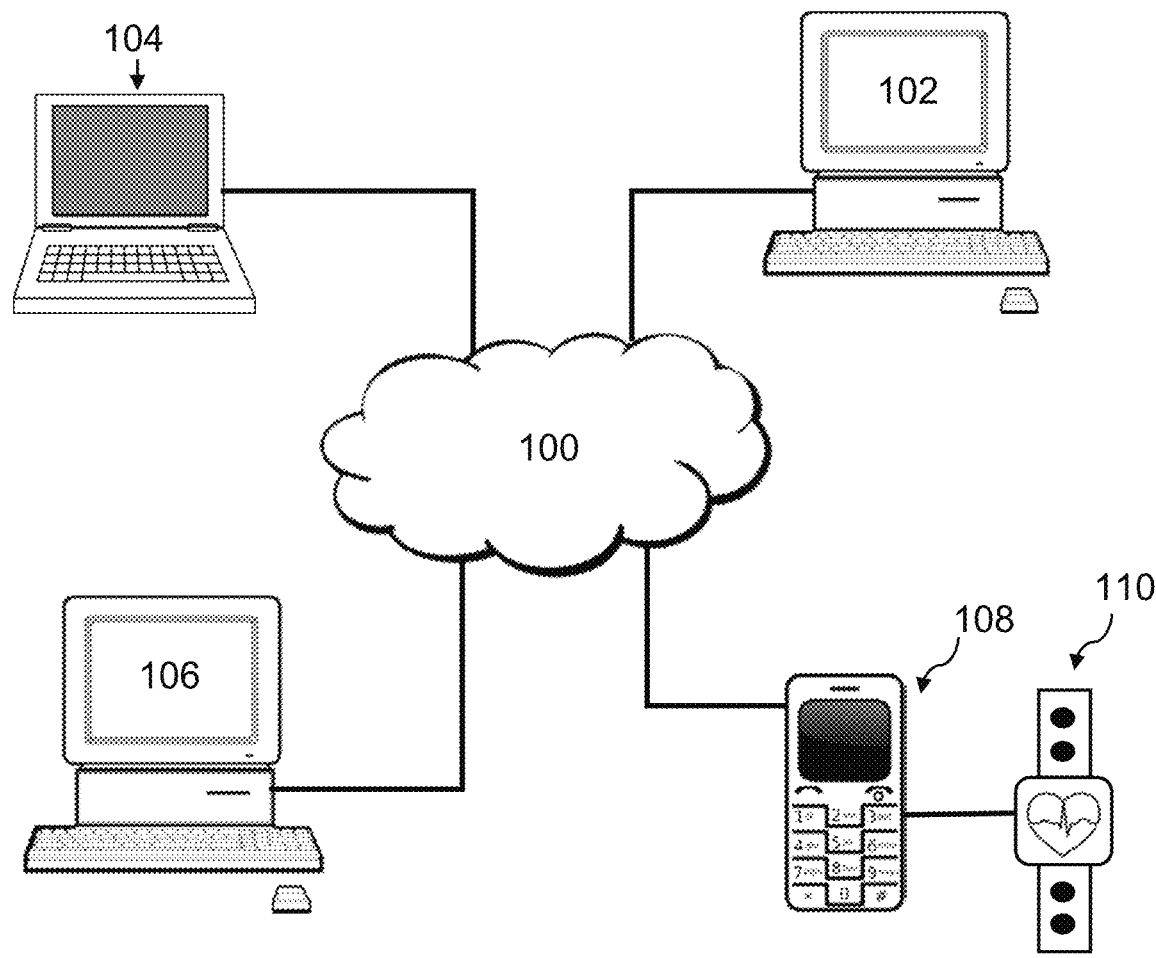
FIG. 1 illustrates a system for using, processing, and displaying biometric data, and for synchronizing biometric data with other data (e.g., video data, audio data, etc.) in accordance with one embodiment of the present invention.

As shown in FIG. 1, a biometric device 110 may be in communication with a computing device 108, such as a smart phone, which, in turn, is in communication with at least one computing device (102, 104, 106) via a wide area network ("WAN") 100, such as the Internet. The computing devices can be of different types, such as a PC, laptop, tablet, smart phone, smart watch etc., using one or different operating systems or platforms. In one embodiment of the present invention, the biometric device 110 is configured to acquire (e.g., measure, sense, estimate, etc.) an individual's heart rate (e.g., biometric data). The biometric data is then provided to the computing device 108, which includes a video and/or audio recorder (not shown).

Figure 3:
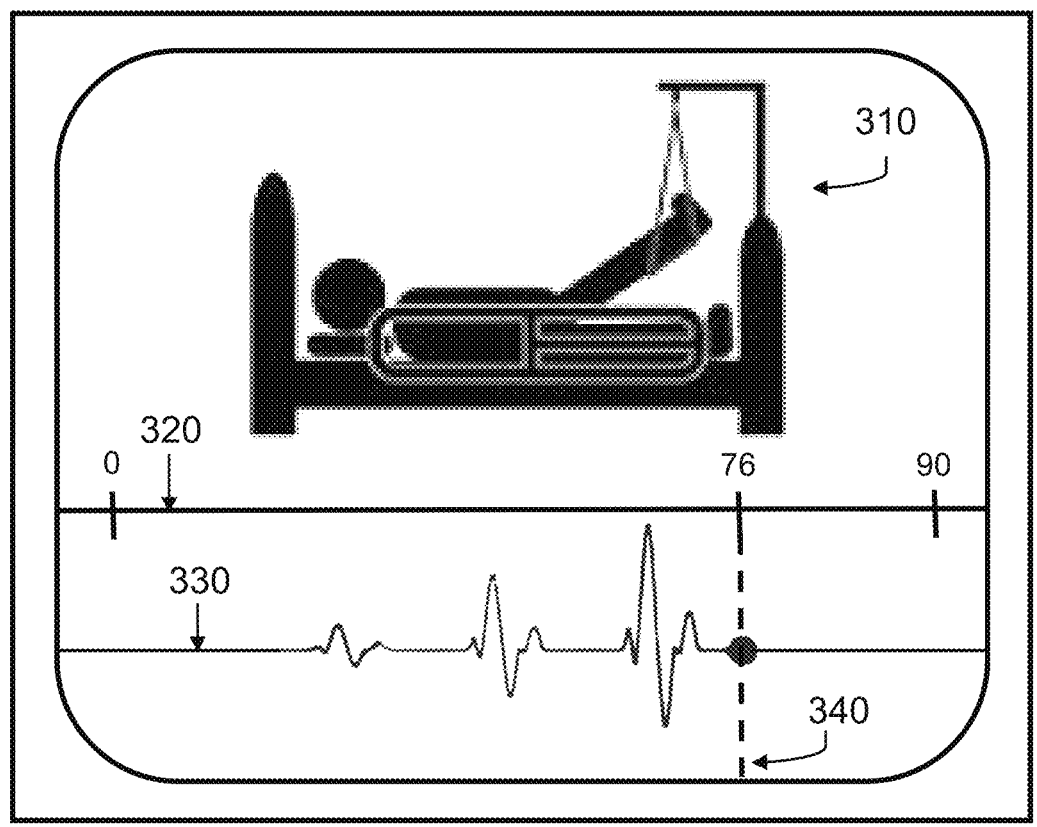
FIG. 3 illustrates an exemplary display of video data synchronized with biometric data in accordance with one embodiment of the present invention.

In a first embodiment of the present invention, the video and/or audio data are provided along with the heart rate data to a host computing device 106 via the network 100. Because the concurrent video and/or audio data and the heart rate data are provided to the host computing device 106, a host application operating thereon (not shown) can be used to synchronize the video data, audio data, and/or heart rate data, thereby allowing a user (e.g., via the user computing devices 102, 104) to view the video data and/or listen to the audio data (either in real-time or time delayed) while viewing the biometric data. For example, as shown in FIG. 3, the host application may use a time-stamp 320, or other sequencing method using metadata, to synchronize the video data 310 with the biometric data 330, allowing a user to view, for example, an individual (e.g., patient in a hospital or at home or other location remote from the hospital or clinic environment, baby in a crib, etc.) at a particular time

340 (e.g., 76 seconds past the start time) and biometric data associated with the individual at that particular time 340 (e.g., 76 seconds past the start time).

It should be appreciated that the host application may further be configured to perform other functions, such as search for a particular activity in video data, audio data, biometric data and/or metadata, and/or ranking video data, audio data, and/or biometric data. For example, the host application may allow the user to search for a particular biometric event, such as a heart rate that has exceeded a particular threshold or value, a heart rate that has dropped below a particular threshold or value, a particular heart rate (or range) for a minimum period of time, etc. By way of another example, the host application may rank video data, audio data, biometric data, or a plurality of synchronized clips (e.g., highlight reels) chronologically, by biometric magnitude (highest to lowest, lowest to highest, etc.), by review (best to worst, worst to best, etc.), or by views (most to least, least to most, etc.). It should further be appreciated that such functions as the ranking, searching, and analysis of data is not limited to a user's individual session, but can be performed across any number of individual sessions of the user, as well as the session or number of sessions of multiple users. One use of this collection of all the various information (video, biometric and other) is to be able to generate sufficient data points for Big Data analysis and Machine Learning of the purposes of generating AI inferences and recommendations.

By way of example, in a clinical or diagnostic context, machine learning algorithms could be used to monitor in near real-time, or search through video data automatically, identifying relevant key occurrences and data. Machine learning algorithms could also be used to search through video data automatically, looking for the most compelling content which could subsequently be stitched together into a short "highlight reel." The neural network could be trained using a plurality of sports videos, along with ratings from users of their level of interest as the videos progress. The input nodes to the network could be a sample of change in intensity of pixels between frames along with the median excitement rating of the current frame. The machine learning algorithms could also be used, in conjunction with a multi-layer convolutional neural network, to automatically classify video content (e.g., what sport is in the video). Once the content is identified, either automatically or manually, algorithms can be used to compare the user's activity to an idealized activity. For example, the system could compare a video recording of the user's golf swing to that of a professional golfer. The system could then provide incremental tips to the user on how the user could improve their swing. Algorithms could also be used to predict fitness levels for users (e.g., if they maintain their program, giving them an incentive to continue working out), match users to other users or practitioners having similar fitness levels, and/or create routines optimized for each user.

Figure 2A:
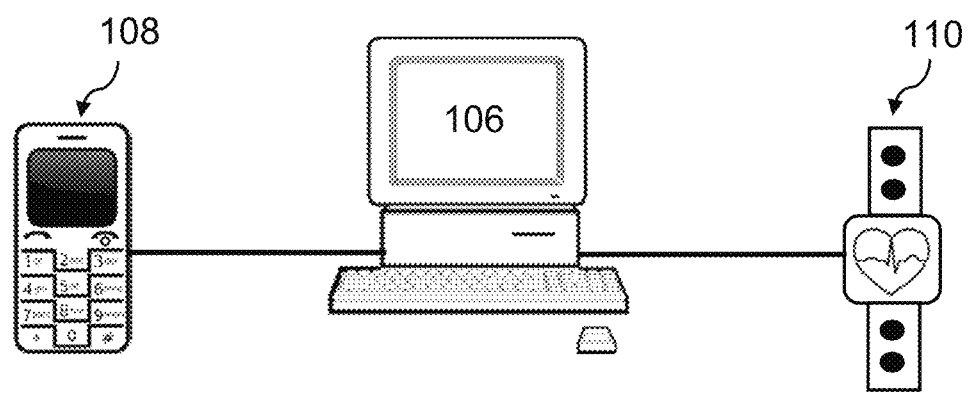
FIG. 2A illustrates a system for using, processing, and displaying biometric data, and for synchronizing biometric data with other data (e.g., video data, audio data, etc.) in accordance with another embodiment of the present invention.

It should also be appreciated, as shown in FIG. 2A, that the biometric data may be provided to the host computing device 106 directly, without going through the computing device 108. For example, the computing device 108 and the biometric device 110 may communicate independently with the host computing device, either directly or via the network 100. It should further be appreciated that the video data, the audio data, and/or the biometric data need not be provided to the host computing device 106 in real-time. For example, video data could be provided at a later time as long as the data can be identified or tied to a particular session. If the video data can be identified, it can then be synchronized to other data (e.g., biometric data) received in real-time.

Figure 2B:
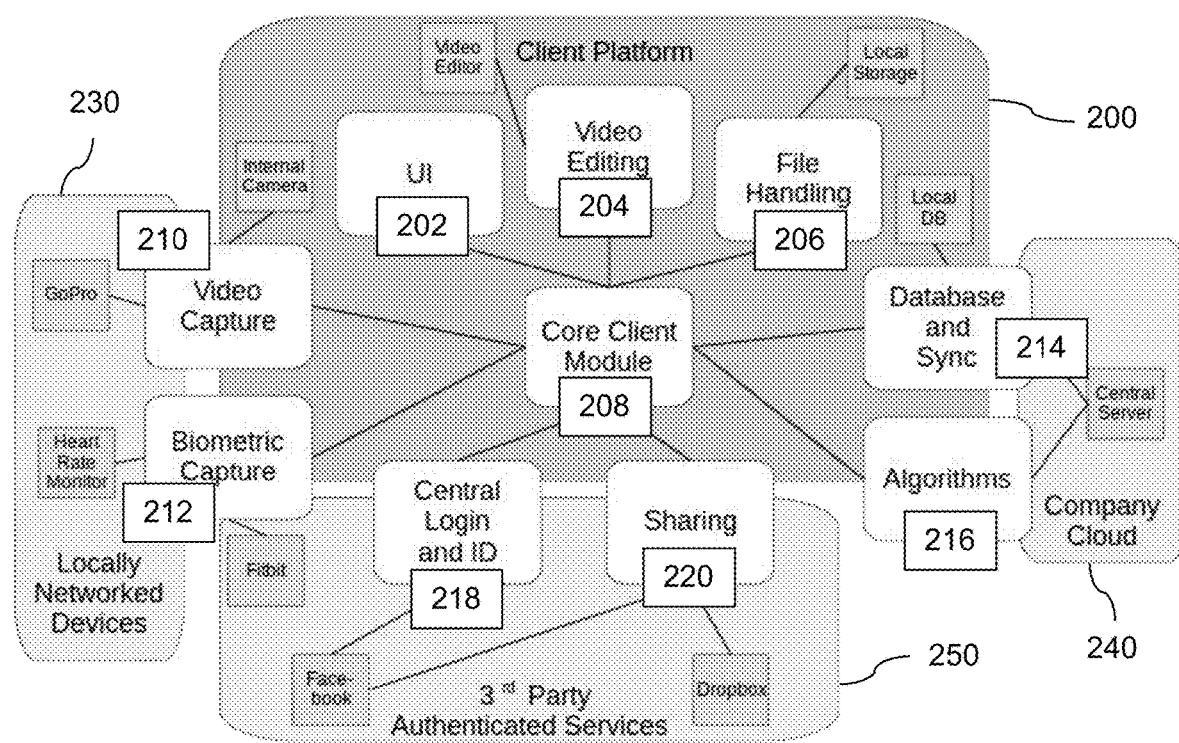
FIG. 2B illustrates a system for using, processing, and displaying biometric data, and for synchronizing biometric data with other data (e.g., video data, audio data, etc.) in accordance with yet another embodiment of the present invention.

In one embodiment of the present invention, as shown in FIG. 2B, the system includes a computing device 200, such as a smart phone, in communication with a plurality of devices, including a host computing device 240 via a WAN (see, e.g., FIG. 1 at 100), third party devices 250 via the WAN (see, e.g., FIG. 1 at 100), and local devices 230 (e.g., via wireless or wired connections). In a preferred embodiment, the computing device 200 downloads a program or application (i.e., client platform) from the host computing device 240 (e.g., company cloud). The client platform includes a plurality of modules that are configured to perform a plurality of functions.

For example, the client platform may include a video capture module 210 for receiving video data from an internal and/or external camera, and a biometric capture module 212 for receiving biometric data from an internal and/or external biometric device. The client platform may also include a user interface module 202, allowing a user to interact with the platform, a video editing module 204 for editing video data, a file handling module 206 for managing (e.g., storing, linking, etc.) data (e.g., video data, biometric data, identification data, start time data, duration data, sample rate data, self-realization data, time-stamp data, etc.), a database and sync module 214 for replicating data (e.g., copying data stored on the computing device 200 to the host computing device 240 and/or copying user data stored on the host computing device 240 to the computing device 200), an algorithm module 216 for processing received data (e.g., synchronizing data, searching/filtering data, creating a highlight reel, etc.), a sharing module 220 for sharing and/or storing data (e.g., video data, highlight reel, etc.) relating either to a single session or multiple sessions, and a central login and ID module 218 for interfacing with third party social media websites, such as Facebook™.

With respect to FIG. 2B, the computing device 200, which may be a smart phone, a tablet, or any other computing device, may be configured to download the client platform from the host computing device 240. Once the client platform is running on the computing device 200, the platform can be used to start a new session, receive video data for the session (i.e., via the video capture module 210) and receive biometric data for the session (i.e., via the biometric capture module 212). This data can be stored in local storage, in a local database, and/or on a remote storage device (e.g., in the company cloud or a third-party cloud, such as Dropbox™, etc.). In a preferred embodiment, the data is stored so that it is linked to information that (i) identifies the session and (ii) enables synchronization.

For example, video data is preferably linked to at least a start time (e.g., a start time of the session) and an identifier. The identifier may be a single number uniquely identifying the session, or a plurality of numbers (e.g., a plurality of globally (or universally) unique identifiers (GUIDs/UUIDs), where a first number uniquely identifying the session and a second number uniquely identifies an activity within the session, allowing a session (e.g., a trip to or an itinerary in a destination, such as Berlin) to include a plurality of activities (e.g., a bike ride, a walk, etc.). By way of example only, an activity (or session) identifier may be a 128 bit identifier that has a high probability of uniqueness, such as 8bf25512-f17a-4e9e-b49a-7c3f59ec1e85). The identifier may also include a session name and/or a session description. Other information about the video data (e.g., video length, video source, etc.) (i.e., "video metadata") can also be stored and linked to the video data. Biometric data is preferably linked to at least the start time (e.g., the same start time linked to the video data), the identifier (e.g., the same identifier linked to the video data), and a sample rate, which identifies the rate at which biometric data is received and/or stored. For example, heart rate data may be received and stored at a rate of thirty samples per minute (30 spm), i.e., once every two seconds, or some other predetermined time interval sample.

In some cases, the sample rate used by the platform may be the sample rate of the biometric device (i.e., the rate at which data is provided by the biometric device). In other cases, the sample rate used by the platform may be independent from the rate at which data is received (e.g., a fixed rate, a configurable rate, etc.). For example, if the biometric device is configured to provide biometric data at a rate of sixty samples per minute (60 spm), the platform may still store the data at a rate of 30 spm. In other words, with a sample rate of 30 spm, the platform will have stored five values after ten seconds, the first value being the second value transmitted by the biometric device, the second value being the fourth value transmitted by the biometric device, and so on. Alternatively, if the biometric device is configured to provide biometric data only when the biometric data changes, the platform may still store the data at a rate of 30 spm. In this case, the first value stored by the platform may be the first value transmitted by the biometric device, the second value stored may be the first value transmitted by the biometric device if at the time of storage no new value has been transmitted by the biometric device, the third value stored may be the second value transmitted by the biometric device if at the time of storage a new value is being transmitted by the biometric device, and so on.

Once the video and biometric data is stored and linked, algorithms can be used to display the data together. For example, if biometric data is stored at a sample rate of 30 spm, which may be fixed or configurable, algorithms (e.g., 216) can be used to display a first biometric value (e.g., below the video data, superimposed over the video data, etc.) at the start of the video clip, a second biometric value two seconds later (two seconds into the video clip), a third biometric value two seconds later (four seconds into the video clip), etc. In alternate embodiments of the present invention, non-video data (e.g., biometric data, self-realization data, etc.) can be stored with a plurality of time-stamps (e.g., individual stamps or offsets for each stored value), which can be used together with the start time to synchronize non-video data to video data.

It should be appreciated that while the client platform can be configured to function autonomously (i.e., independent of the host network device 240), in one embodiment of the present invention, certain functions of the client platform are performed by the host network device 240, and can only be performed when the computing device 200 is in communication with the host computing device 240. Such an embodiment is advantageous in that it not only offloads certain functions to the host computing device 240, but it ensures that these functions can only be performed by the host computing device 240 (e.g., requiring a user to subscribe to a cloud service in order to perform certain functions). Functions offloaded to the cloud may include functions that are necessary to display non-video data together with video data (e.g., the linking of information to video data, the linking of information to non-video data, synchronizing non-video data to video data, etc.), or may include more advanced functions, such as generating and/or sharing a "highlight reel." In alternate embodiments, the computing device 200 is configured to perform the foregoing functions as long as certain criteria has been met. This criteria may include the computing device 200 being in communication with the host computing device 240, or the computing device 200 previously being in communication with the host computing device 240 and the period of time since the last communication being equal to or less than a predetermined amount of time. Technology known to those skilled in the art (e.g., using a keyed hash-based method authentication code (HMAC), a stored time of said last communication (allowing said computing device to determine whether said delta is less than a predetermined amount of time), etc.) can be used to ensure that this criteria is met before allowing the performance of certain functions.

Figure 5:
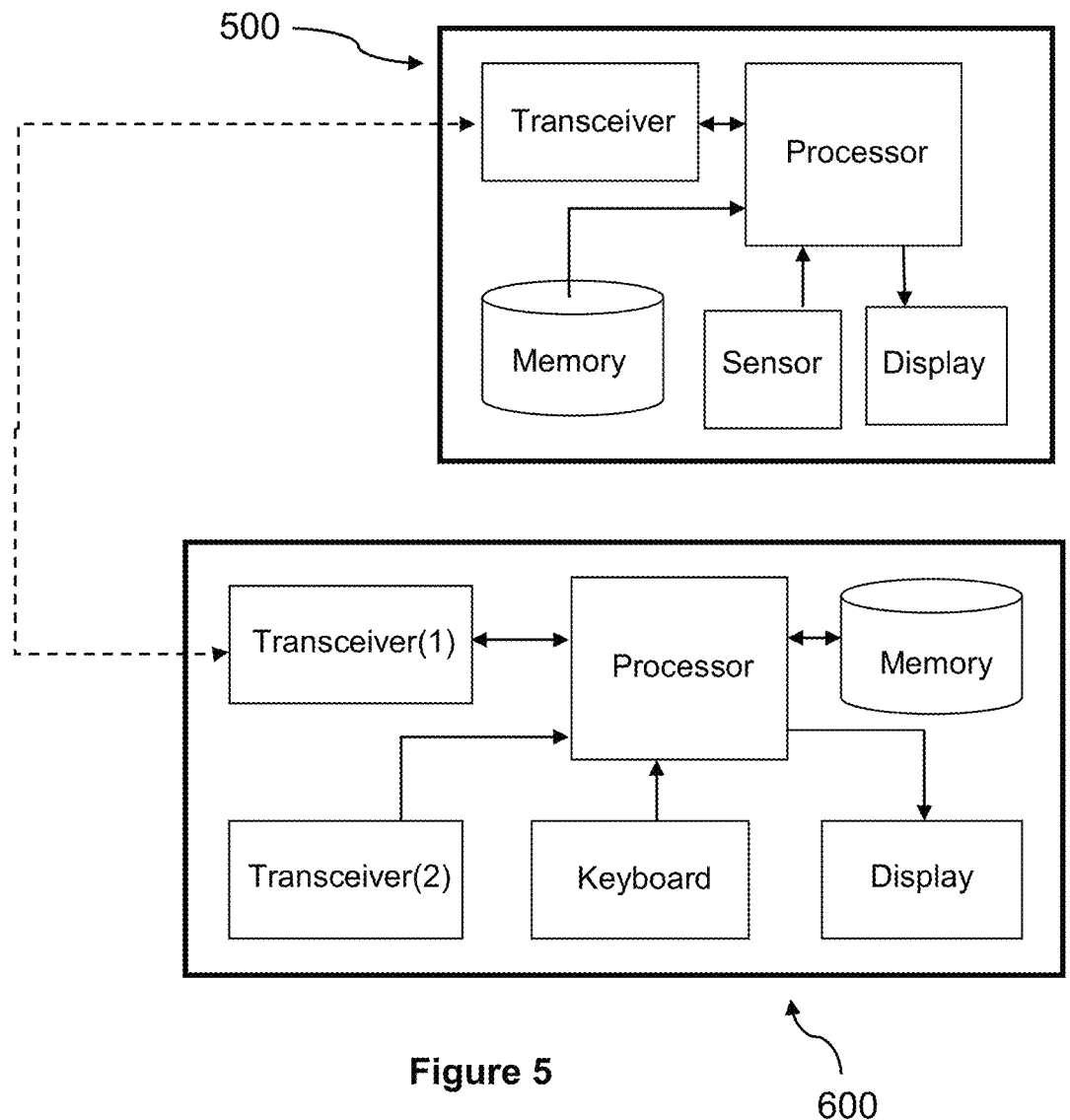
FIG. 5 illustrates a block diagram for using, processing, and displaying biometric data, and for synchronizing biometric data with other data (e.g., video data, audio data, etc.) in accordance with another embodiment of the present invention.

Block diagrams of an exemplary computing device and an exemplary biometric device are shown in FIG. 5. In particular, the exemplary biometric device 500 includes a sensor for sensing biometric data, a display for interfacing with the user and displaying various information (e.g., biometric data, set-up data, operation data, such as start, stop, and pause, etc.), a memory for storing the sensed biometric data, a transceiver for communicating with the exemplary computing device 600, and a processor for operating and/or driving the transceiver, memory, sensor, and display. The exemplary computing device 600 includes a transceiver(1) for receiving biometric data from the exemplary biometric device 500 (e.g., using any of telemetry, any WiFi standard, DNLA, Apple AirPlay, Bluetooth, near field communication (NFC), RFID, ZigBee, Z-Wave, Thread, Cellular, a wired connection, infrared or other method of data transmission, datacasting or streaming, etc.), a memory for storing the biometric data, a display for interfacing with the user and displaying various information (e.g., biometric data, set-up data, operation data, such as start, stop, and pause, input in-session comments or add voice notes, etc.), a keyboard for receiving user input data, a transceiver(2) for providing the biometric data to the host computing device via the Internet (e.g., using any of telemetry, any WiFi standard, DNLA, Apple AirPlay, Bluetooth, near field communication (NFC), RFID, ZigBee, Z-Wave, Thread, Cellular, a wired connection, infrared or other method of data transmission, datacasting or streaming, etc.), and a processor for operating and/or driving the transceiver(1), transceiver (2), keyboard, display, and memory.

The keyboard in the computing device 600, or alternatively the keyboard in biometric device 500, may be used to enter self-realization data, or data on how the user is feeling at a particular time. For example, if the user is feeling tired, the user may hit the "T" button on the keyboard. If the user is feeling their endorphins kick in, the user may hit the "E" button on the keyboard. And if the user is getting their second wind, the user may hit the "S" button on the keyboard. This data is then stored and linked to either a sample rate (like biometric data) or time-stamp data, which may be a time or an offset to the start time that each button was pressed. This would allow the self-realization data, in the same way as the biometric data, to be synchronized to the video data. It would also allow the self-realization data, like the biometric data, to be searched or filtered (e.g., in order to find video corresponding to a particular event, such as when the user started to feel tired, etc.).

Figure 4:
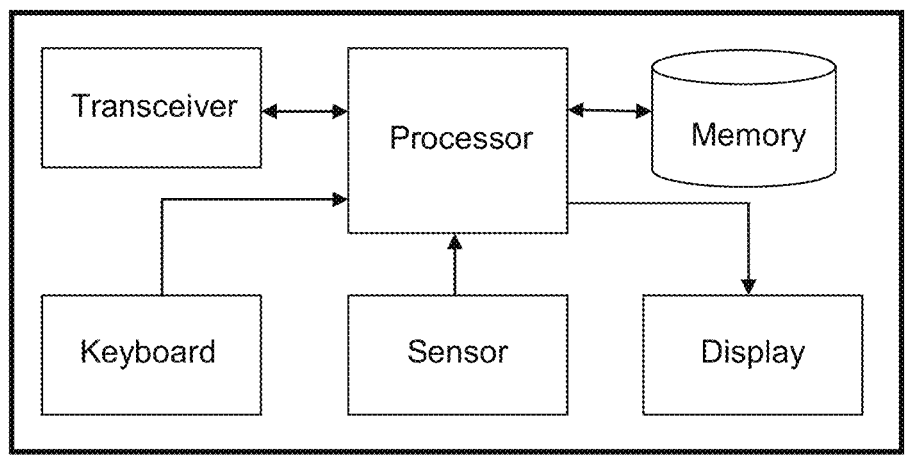
FIG. 4 illustrates a block diagram for using, processing, and displaying biometric data, and for synchronizing biometric data with other data (e.g., video data, audio data, etc.) in accordance with one embodiment of the present invention.

It should be appreciated that the present invention is not limited to the block diagrams shown in FIG. 5, and a biometric device and/or a computing device that includes fewer or more components is within the spirit and scope of the present invention. For example, a biometric device that does not include a display, or includes a camera and/or microphone is within the spirit and scope of the present invention, as are other data-entry devices or methods beyond a keyboard, such as a touch screen, digital pen, voice/audible recognition device, gesture recognition device, so-called "wearable," or any other recognition device generally known to those skilled in the art. Similarly, a computing device that only includes one transceiver, further includes a camera (for capturing video) and/or microphone (for capturing audio or for performing spatial analytics through recording or measurement of sound and how it travels), or further includes a sensor (see FIG. 4) is within the spirit and scope of the present invention. It should also be appreciated that self-realization data is not limited to how a user feels, but could also include an event that the user or the application desires to memorialize. For example, the user may want to record (or time-stamp) the user biking past wildlife, or a particular architectural structure, or the application may want to record (or time-stamp) a patient pressing a "request nurse" button, or any other sensed non-biometric activity of the user.

Referring back to FIG. 1, as discussed above in conjunction with FIG. 2B, the host application (or client platform) may operate on the computing device 108. In this embodiment, the computing device 108 (e.g., a smart phone) may be configured to receive biometric data from the biometric device 110 (either in real-time, or at a later stage, with a time-stamp corresponding to the occurrence of the biometric data), and to synchronize the biometric data with the video data and/or the audio data recorded by the computing device 108 (or a camera and/or microphone operating thereon). It should be appreciated that in this embodiment of the present invention, other than the host application being run locally (e.g., on the computing device 108), the host application (or client platform) operates as previously discussed.

Again, with reference to FIG. 1, in another embodiment of the present invention, the computing device 108 further includes a sensor for sensing biometric data. In this embodiment of the present invention, the host application (or client platform) operates as previously discussed (locally on the computing device 108), and functions to at least synchronize the video, audio, and/or biometric data, and allow the synchronized data to be played or presented to a user (e.g., via a display portion, via a display device connected directly to the computing device, via a user computing device connected to the computing device (e.g., directly, via the network, etc.), etc.).

It should be appreciated that the present invention, in any embodiment, is not limited to the computing devices (number or type) shown in FIGS. 1 and 2, and may include any of a computing, sensing, digital recording, GPS or otherwise location-enabled device (for example, using WiFi Positioning Systems "WPS", "AGPS" or other forms of deriving geographical location, such as through network triangulation), generally known to those skilled in the art, such as a personal computer, a server, a laptop, a tablet, a smart phone, a cellular phone, a smart watch, an activity band, a heart-rate strap, a mattress sensor, a shoe sole sensor, a digital camera, a near field sensor or sensing device, etc. It should also be appreciated that the present invention is not limited to any particular biometric device, and includes biometric devices that are configured to be worn on the wrist (e.g., like a watch), worn on the skin (e.g., like a skin patch) or scalp, or incorporated into computing devices (e.g., smart phones, etc.), either integrated in, or added to items such as bedding, wearable devices such as clothing, footwear, helmets or hats, or ear phones, or athletic equipment such as rackets, golf clubs, or bicycles, where other kinds of data, including physical performance metrics such as racket or club head speed, or pedal rotation/second, or footwear recording such things as impact zones, gait or shear, can also be measured synchronously with biometrics, and synchronized to video. Other data can also be measured synchronously with video data, including biometrics on animals (e.g., a bull's acceleration or pivot or buck in a bull riding event, a horse's acceleration matched to heart rate in a horse race, etc.), and physical performance metrics of inanimate objects, such a revolutions/minute (e.g., in a vehicle, such as an automobile, a motorcycle, etc.), miles/hour (or the like) (e.g., in a vehicle, such as an automobile, a motorcycle, etc., a bicycle, etc.), or G-forces (e.g., experienced by the user, an animal, and inanimate object, etc.). All of this data (collectively "non-video data," which may include metadata, or data on non-video data) can be synchronized to video data using a sample rate and/or at least one time-stamp, as discussed above.

Figure 7:
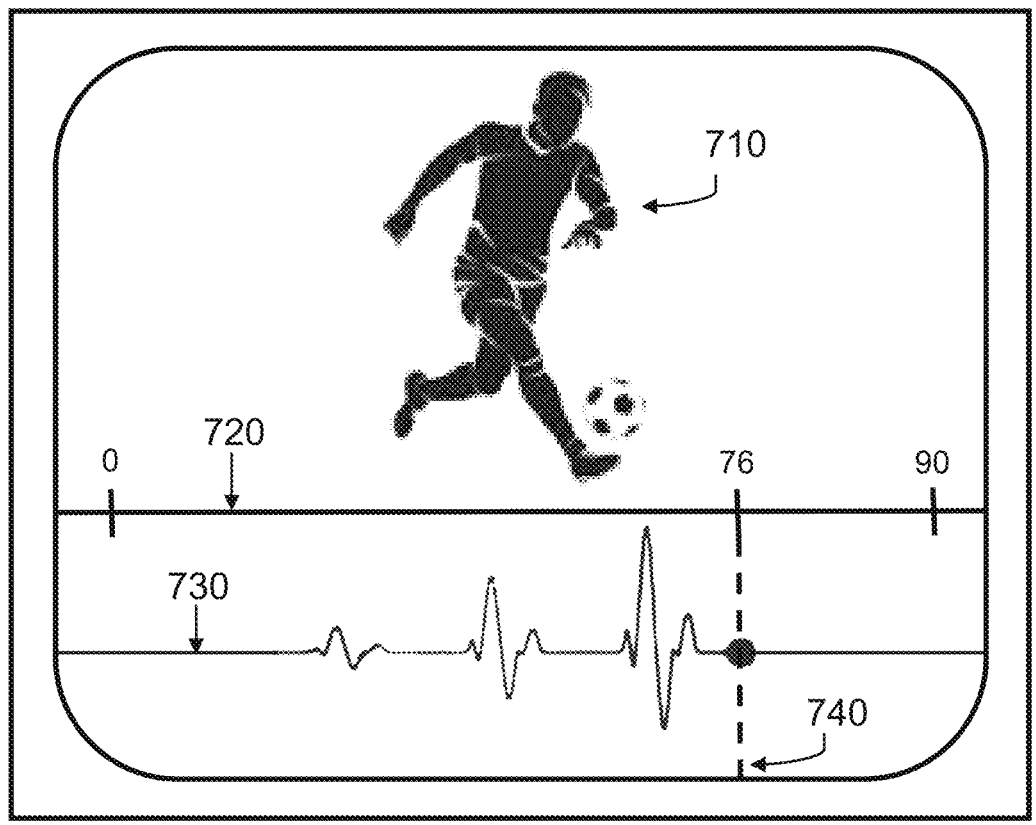
FIG. 7 illustrates an exemplary display of video data synchronized with biometric data in accordance with another embodiment of the present invention.

It should further be appreciated that the present invention need not operate in conjunction with a network, such as the Internet. For example, as shown in FIG. 2A, the biometric device 110, which may be, for example, be a wireless activity band for sensing heart rate, and the computing device 108, which may be, for example, a digital video recorder, may be connected directly to the host computing device 106 running the host application (not shown), where the host application functions as previously discussed. In this embodiment, the video, audio, and/or biometric data can be provided to the host application either (i) in real time, or (ii) at a later time, since the data is synchronized with a sample rate and/or time-stamp. This would allow, for example, at least video of an athlete, or a sportsman or woman (e.g., a football player, a soccer player, a racing driver, etc.) to be shown in action (e.g., playing football, playing soccer, motor racing, etc.) along with biometric data of the athlete in action (see, e.g., FIG. 7). By way of example only, this would allow a user to view a soccer player's heart rate 730 as the soccer player dribbles a ball, kicks the ball, heads the ball, etc. This can be accomplished using a time stamp 720 (e.g., start time, etc.), or other sequencing method using metadata (e.g., sample rate, etc.), to synchronize the video data 710 with the biometric data 730, allowing the user to view the soccer player at a particular time 740 (e.g., 76 seconds) and biometric data associated with the athlete at that particular time 340 (e.g., 76 seconds). Similar technology can be used to display biometric data on other athletes, card players, actors, online gamers, etc.

Where it is desirable to monitor or watch more than one individual from a camera view, for example, patients in a hospital ward being observed from a remote nursing station or, during a televised broadcast of a sporting event such as a football game, with multiple players on the sports field, the system can be so configured, by the subjects using Bluetooth or other wearable or NFC sensors (in some cases with their sensing capability also being location-enabled in order to identify which specific individual to track) capable of transmitting their biometrics over practicable distances, in conjunction with relays or beacons if necessary, such that the viewer can switch the selection of which of one or multiple individuals' biometric data to track, alongside the video or broadcast, and, if wanted and where possible within the limitations of the video capture field of the camera used, also to concentrate the view of the video camera on a reduced group or on a specific individual. In an alternate embodiment of the present invention, selection of biometric data is automatically accomplished, for example, based on the individual's location in the video frame (e.g., center of the frame), rate of movement (e.g., moving quicker than other individuals), or proximity to a sensor (e.g., being worn by the individual, embedded in the ball being carried by the individual, etc.), which may be previously activate or activated by a remote radio frequency signal. Activation of the sensor may result in biometric data of the individual being transmitted to a receiver, or may allow the receiver to identified biometric data of the individual amongst other data being transmitted (e.g., biometric data from other individuals).

In the context of fitness or sports tracking, it should be appreciated that the capturing of an individual's activity on video is not dependent on the presence of a third party to do this, but various methods of self-videoing can be envisaged, such as a video capture device mounted on the subject's wrist or a body harness, or on a selfie attachment or a gimbal, or fixed to an object (e.g., sports equipment such as bicycle handlebars, objects found in sporting environments such as a basketball or tennis net, a football goal post, a ceiling, etc., a drone-borne camera following the individual, a tripod, etc.). It should be further noted that such video capture devices can include more than one camera lens, such that not only the individual's activity may be videoed, but also simultaneously a different view, such as what the individual is watching or sees in front of them (i.e., the user's surroundings). The video capture device could also be fitted with a convex mirror lens, or have a convex mirror added as an attachment on the front of the lens, or be a full 360 degree camera, or multiple 360 cameras linked together, such that either with or without the use of specialized software known in the art, a 360 degree all-around or surround view can be generated, or a 360 global view in all axes can be generated.

In the context of augmented or virtual reality, where the individual is wearing suitably equipped augmented reality ("AR") or virtual reality ("VR") glasses, goggles, headset or is equipped with another type of viewing display capable of rendering AR, VR, or other synthesized or real 3D imagery, the biometric data such as heart rate from the sensor, together with other data such as, for example, work-out run or speed, from a suitably equipped sensor, such as an accelerometer capable of measuring motion and velocity, could be viewable by the individual, superimposed on their viewing field. Additionally an avatar of the individual in motion could be superimposed in front of the individual's viewing field, such that they could monitor or improve their exercise performance, or otherwise enhance the experience of the activity by viewing themselves or their own avatar, together (e.g., synchronized) with their performance (e.g., biometric data, etc.). Optionally, the biometric data also of their avatar, or the competing avatar, could be simultaneously displayed in the viewing field. In addition (or alternatively), at least one additional training or competing avatar can be superimposed on the individual's view, which may show the competing avatar(s) in relation to the individual (e.g., showing them superimposed in front of the individual, showing them superimposed to the side of the user, showing them behind the individual (e.g., in a rear-view-mirror portion of the display, etc.), and/or showing them in relation to the individual (e.g., as blips on a radar-screen portion of the display, etc.), etc. Competing avatar(s), either of real people such as their friends or training acquaintances, can be used to motivate the user to improve or correct their performance and/or to make their exercise routine more interesting (e.g., by allowing the individual to "compete" in the AR, VR, or Mixed Reality ("MR") environment while exercising, or training, or virtually "gamifying" their activity through the visualization of virtual destinations or locations, imagined or real, such as historical sites, scanned or synthetically created through computer modeling).

Additionally, any multimedia sources to which the user is being exposed whilst engaging in the activity which is being tracked and recorded, should similarly be able to be recorded with the time stamp, for analysis and/or correlation of the individual's biometric response. An example of an application of this could be in the selection of specific music tracks for when someone is carrying out a training activity, where the correlation of the individual's past response, based, for example, on heart rate (and how well they achieved specific performance levels or objectives) to music type (e.g., the specific music track(s), a track(s) similar to the specific track(s), a track(s) recommended or selected by others who have listened to or liked the specific track(s), etc.) is used to develop a personalized algorithm, in order to optimize automated music selection to either enhance the physical effort, or to maximize recovery during and after exertion. The individual could further specify that they wished for the specific track or music type, based upon the personalized selection algorithm, to be played based upon their geographical location; an example of this would be someone who frequently or regularly uses a particular circuit for training or recreational purposes. Alternatively, tracks or types of music could be selected through recording or correlation of past biometric response in conjunction with self-realization inputting when particular tracks were being listened to.

It should be appreciated that biometric data does not need to be linked to physical movement or sporting activity, but may instead be combined with video of an individual at a fixed location (e.g., where the individual is being monitored remotely or recorded for subsequent review), for example, as shown in FIG. 3, for health reasons or a medical condition, such as in their home or in hospital, or a senior citizen in an assisted-living environment, or a sleeping infant being monitored by parents whilst in another room or location.

Alternatively, the individual might be driving past or in the proximity of a park or a shopping mall, with their location being recorded, typically by geo-stamping, or additional information being added by geo-tagging, such as the altitude or weather at the specific location, together with what the information or content is, being viewed or interacted with by the individual (e.g., a particular advertisement, a movie trailer, a dating profile, etc.) on the Internet or a smart/enabled television, or on any other networked device incorporating a screen, and their interaction with that information or content, being viewable or recorded by video, in conjunction with their biometric data, with all these sources of data being able to be synchronized for review, by virtue of each of these individual sources being time-stamped or the like (e.g., sampled, etc.). This would allow a third party (e.g., a service provider, an advertiser, a provider of advertisements, a movie production company/promoter, a poster of a dating profile, a dating site, etc.) to acquire for analysis of their response, the biometric data associated with the viewing of certain data by the viewer, where either the viewer or their profile could optionally be identifiable by the third party's system, or where only the identity of the viewer's interacting device is known, or can be acquired from the biometric sending party's GPS, or otherwise location-enabled, device.

For example, an advertiser or an advertisement provider could see how people are responding to an advertisement, or a movie production company/promoter could evaluate how people are responding to a movie trailer, or a poster of a dating profile or the dating site itself, could see how people are responding to the dating profile. Alternatively, viewers of online players of an online gaming or eSports broadcast service such as twitch.tv, or of a televised or streamed online poker game, could view the active participants' biometric data simultaneously with the primary video source as well as the participants' visible reactions or performance. As with video/audio, this can either be synchronized in real-time, or synchronized later using the embedded time-stamp or the like (e.g., sample rate, etc.). Additionally, where facial expression analysis is being generated from the source video, for example in the context of measuring an individual's response to advertising messages, since the video is already time-stamped (e.g., with a start time), the facial expression data can be synchronized and correlated to the physical biometric data of the individual, which has similarly been time-stamped and/or sampled, As previously discussed, the host application may be configured to perform a plurality of functions. For example, the host application may be configured to synchronize video and/or audio data with biometric data. This would allow, for example, an individual watching a sporting event (e.g., on a TV, computer screen, etc.) to watch how each player's biometric data changes during play of the sporting event, or also to map those biometric data changes to other players or other comparison models. Similarly, a doctor, nurse, or medical technician could record a person's sleep habits, and watch, search or later review, the recording (e.g., on a TV, computer screen, etc.)

while monitoring the person's biometric data. The system could also use machine learning to build a profile for each patient, identifying certain characteristics of the patient (e.g., their heart rate rhythm, their breathing pattern, etc.) and notify a doctor, a nurse, or medical technician or trigger an alarm if the measured characteristics appear abnormal or irregular.

The host application could also be configured to provide biometric data to a remote user via a network, such as the Internet. For example, a biometric device (e.g., a smart phone with a blood-alcohol sensor) could be used to measure a person's blood-alcohol level (e.g., while the person is talking to the remote user via the smart phone), and to provide the person's blood-alcohol level to the remote user. By placing the sensor near, or incorporating it in the microphone, such a system would allow a parent to determine whether their child has been drinking alcohol by participating in a telephone or video call with their child. Different sensors known in the art could be used to sense different chemicals in the person's breath, or detect people's breathing patterns through analysis of sound and speed variations, allowing the monitoring party to determine whether the subject has been using alcohol or other controlled substances or to conduct breath analysis for other diagnostic reasons including respiratory rate measurement.

The system could also be adapted with a so-called "lab on a chip" (LOC) integrated in the device itself, or with a suitable attachment added to it, for the remote testing for example, of blood samples where the smart-phone is either used for the collection and sending of the sample to a testing laboratory for analysis, or is used to carry out the sample collection and analysis within the device itself. In either case the system is adapted such that the identity of the subject and their blood sample are cross-authenticated for the purposes of sample and analysis integrity as well as patient identity certainty, through the simultaneous recording of the time-stamped video and time and/or location (or GPS) stamping of the sample at the point of collection and/or submission of the sample. This confirmation of identity is particularly important for regulatory, record keeping and health insurance reasons in the context of telemedicine, since the individual will increasingly be performing functions which, till now, have been carried out typically on-site at the relevant facility, by qualified and regulated medical or laboratory staff, rather than by the subject using a networked device, either for upload to the central analysis facility, or for remote analysis on the device itself.

This, or the collection of other biometric data such as heart rate or blood pressure, could also be applied in situations where it is critical for safety reasons, to check, via regular remote video monitoring in real time, whether say a pilot of a plane, a truck or train driver, are in fit and sound condition to be in control of their vehicle or vessel or whether for example they are experiencing a sudden incapacity or heart attack etc. Because the monitored person is being videoed at the same time as providing time-stamped, geo-stamped and/or sampled biometric data, there is less possibility for the monitored person or a third party, to "trick", "spoof" or bypass the system. In a patient/doctor remote consultation setting, the system could be used for secure video consults where also, from a regulatory or health insurance perspective, the consultation and its occurrence is validated through the time and/or geo stamp validation. Furthermore, where there is a requirement for a higher level of authentication, the system could further be adapted to use facial recognition or biometric algorithms, to ensure that the correct person is being monitored, or facial expression analysis could be used for behavioral pattern assessment.

The present invention can also be used to address concerns with the current COVID-19 (coronavirus) pandemic. One of the most immediate consequences of the pandemic for medical staff and health services has been the increased burden of carrying out diagnostic checks on patients. In one embodiment, the present invention could be used to provide telemedicine services, allowing diagnostic checks (e.g., health and wellness testing, coronavirus testing, etc.) to be conducted in a safe, reliable, and convenient manner, and to do so more efficiently and with reduced risk of infection exposure both for patients and medical staff. This could be achieved on a scalable basis through providing the patients with a system utilizing a mobile computing device (e.g., smartphone, tablet, etc.) to securely record their vital signs and then transmit them to the relevant medical services. Such a system would be readily accessible for the patients reporting their vital signs, as well as for the medical staff monitoring those patients.

As discussed above, the system could be utilized both pre- and post-hospitalization or treatment. In a pre-hospitalization context, where individuals are experiencing symptoms, or have already been in contact with medical services and not yet been (or needed to be) hospitalized but are nevertheless in need of regular observation for any change in their condition, this would allow for consistent and timely monitoring of the patients' vital signs. Once the vital signs are recorded, the data can be uploaded automatically to the medical services. In a post-hospitalization utilization, if the patient is considered well enough to continue recovery and convalescence at home, it could allow for an earlier discharge from hospital (freeing up hospital beds), while still having the patient's condition monitored without having to rely on medical staff physically collecting their vital signs. In both cases, the vital signs could be uploaded to the cloud so that the medical services have a digitalized record of the evolution of that data, as well as being able to integrate it in the patient record keeping system or electronic health record (EHR).

This evolution of data (e.g., collecting vital signs from a single patient over a period of days, weeks, months, etc.) can be used to determine whether a treated patient (e.g., diagnosed with COVID-19) is getting better or worse, or provide a benchmark for the patient, or their vital signs, prior to being diagnosed with an illness. For example, in order to evaluate pulse oximeter data, it may be necessary to review previous pulse oximeter data (i.e., when they were healthy, or at least not suffering from the illness-at-issue). Thus, while pulse oximeter data (in and of itself) may be evaluated to help determine whether a patient is suffering from an illness, it may be beneficial to analyze the current pulse oximeter data in conjunction with prior pulse oximeter data (e.g., from months ago), or a differential thereof (i.e., a different between the prior reading and the current reading), or a combination thereof, to help determine whether the patient is suffering from an illness. The evolution of data could also be used in the aggregate, to determine trends with respect to particular illnesses, ailments, general health, or wellbeing.

Figure 30:
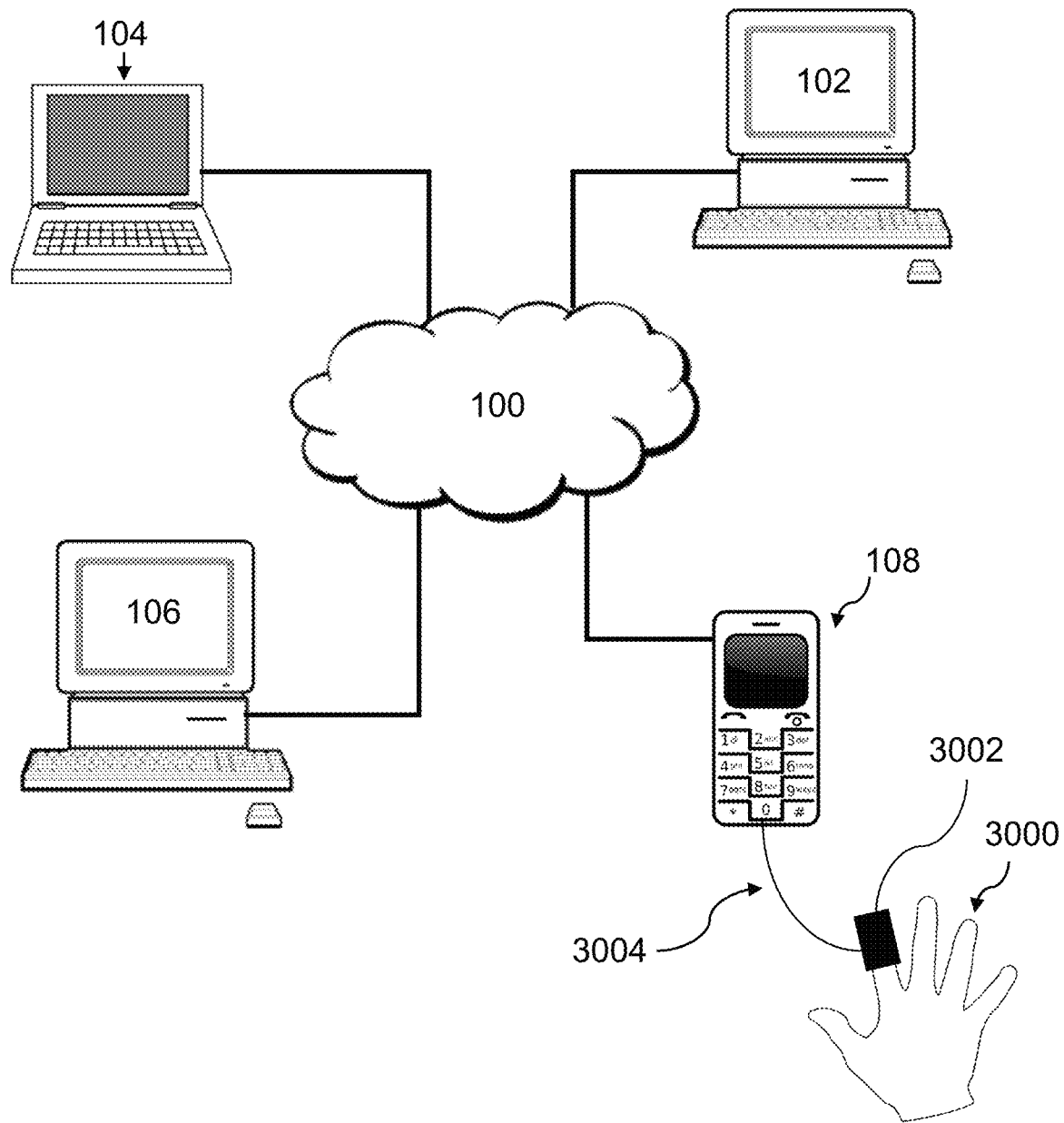
FIG. 30 illustrates a system for acquiring, processing, and using biometric data (e.g., vital signs, etc.) in accordance with another embodiment of the present invention.

Such a system in shown in FIG. 30, which is identical (structurally and functionally) to the system shown in FIG. 1. In FIG. 30, however, the communication device 108 is further (or alternatively) in communication with a pulse oximeter 3002, which may be configured to be worn over a patient's finger 3000. (Note that dependent on the type of oximeter used it can be placed on a patient's ear lobe or other extremity, or worn on a wrist such as in a fitness band or smartwatch). As with the biometric device 110 shown in FIG. 1, the pulse oximeter 3002 may communicate with the communication device 108 via a wired and/or wireless (e.g., Bluetooth, NFC, etc.) communication channel 3004. This channel may be used to provide pulse oximeter data to the communication device 108 over a particular period of time (typically determined via the communication device 108 or an application operating thereon). This may include, but is not limited to, pulse (bpmPR) and blood oxygen saturation level (or percentage) ($SpO_2$).

It should be appreciated that other vital signs may be acquired (e.g., automatically (e.g., via at least one sensor) or manually (e.g., by requiring the user to enter the information), including, but not limited to respiratory rate (e.g., number of breaths per minute), body temperature, and blood pressure (e.g., systolic pressure, diastolic pressure), and used together with (or to calculate) other values, such as perfusion Index (PI %), perfusion Index Trend Waveform, age, weight, sex, etc., to determine the patient's health, wellness, and/or wellbeing (e.g., whether the patient is suffering from a bacterial and/or viral infection, etc.). It should be appreciated that this determination can be made manually (e.g., by a doctor, technician, etc.) or automatically (e.g., using software, artificial intelligence, etc.), and (i) in isolation, (ii) by comparing measured data to at least one known value (e.g., values indicative of COVID-19, etc.), or (iii) by comparing measured data with previously patient data to determine a differential and comparing the differential to at least one known value (e.g., values indicative of COVID-19, etc.).

Depending on the specific requirements of the medical service (hospital, doctor etc.) the incoming data can be used to alert the medical staff of any change in vital signs (or determination) requiring an action to be taken. Subject to the prevailing patient privacy regulations, the data could either be held on a trusted third-party server, such as that operated by the system provider, or sent directly to the medical services' portal without transiting through another server.

The recording of the vital signs is preferably done through the communication device 108 (e.g., smartphone, etc.), or an application operating thereon, using a simple user interface. Once the application is downloaded and installed on the communication device 108, the application may start a first-time set-up process by checking that Internet connectivity through Wi-Fi and/or the wireless cellular network is established. The credentials of the patient may then be verified, and their unique ID confirmed (note that the system and the application should be GDPR and HIPPA compliant, as well as having choice of language e.g. English, Spanish, German, etc.). There may be an option for the patient to view a symptoms list/checker and to enter any other observations which may be of relevance for medical or monitoring staff as well as self-realization measures of their perceived state of health or physical condition. Also, in the case of monitoring for other conditions such as sleep disorders like sleep apnea, which can be screened by using oximetry data, other elements could be noted such as the number of hours slept or the perceived quality of sleep In a preferred embodiment, the patient would then switch the pulse oximeter 3002 on and establishes a wireless (e.g., Bluetooth) connection with the communication device 108. This is verified by the application and confirms to the patient that the system is configured and operating correctly. The patient may be informed that for future use, both Bluetooth and data network connectivity must be enabled on the phone when using the vital signs reporting system.

The patient would then begin a vital signs data session, which may include: (1) taking their temperature and manually entering it into the application; (2) measuring their respiratory rate (RR) using the timer viewer within the application over a predetermined time period (increments of 30 seconds upwards) (note, the application may automatically calculate breaths per minute from the entered information); (3) attaching the pulse oximeter (e.g., placing onto their pointer finger); vital signs (e.g., $SpO_2$, bpmPR, PI %, Perfusion Index Trend Waveform, etc.) are recorded; (5) confirming to the patient that the information is complete and ready to be sent; (6) allowing the patient to transmit the data into the cloud (e.g., host); (7) confirming that the data has been successfully uploaded and/or received; (8) setting a reminder within the application for when next to record and send the vital signs; and (9) optionally enabling a return-loop messaging system from the medical monitoring staff back to the patient over the mobile phone application depending on regulatory provisions.

At the monitoring end, where the data is viewable, an alert system can be enabled, but this is dependent both on the preferences of the medical staff and also on the specific regulatory framework as to where the data is stored and what happens to the data afterwards. Alerts can be provided to medical staff and/or the patient and may be based on the data itself, a change in the data, or a determination based on the data, where the determination is made either manually or automatically, as discussed above.

It should be appreciated that the present invention is not limited to the foregoing method and may involve additional, fewer, or different steps. For example, certain data (e.g., temperature, etc.) could be acquired manually and/or automatically (e.g., via a temperature sensor, blood pressure sensor, respiratory rate sensor, etc., where the devices used for acquiring the biometric data, such as a thermometer for body temperature readings, are similarly connected by Bluetooth or some other connection protocol, or physically, to the smartphone or other such storage and network device.). By way of another example, other biometric data could be measured and/or entered (or acquired) to determine whether a particular medical condition (e.g., COVID-19, etc.) is present, including, for example, $CO_2$ levels, blood glucose, ambient conditions (temperature, humidity, light levels, altitude, and barometric pressure), heart rate variance (HRV), EKG data, perspiration levels, ketones, blood content, saliva content, audible levels, brain waves (e.g., EEG) and/or activity or other neurological measurements, physical characteristics (e.g., weight, etc.) or responses (e.g., facial changes, iris (or pupil) changes, voice (or tone) changes, etc.), or any combination or resultant thereof.

As discussed above, software or artificial intelligent (AI) can be used to make a medical diagnosis based on the received information. This may require normalization or adjusting the data received over a period of time (and/or external data) to then be compared to known values to determine whether, or the likelihood that the individual suffers from a particular medical condition (e.g. COVID-19, etc.). The results provided to the individual could be an indication (e.g., positive, negative) or the likelihood (e.g., 1-10, low, medium, high) of the medical condition. The results could then be provided to the individual and/or to a third party (e.g., to a hospital, confirming a medical condition and/or the likelihood thereof, etc.).

Figure 31:
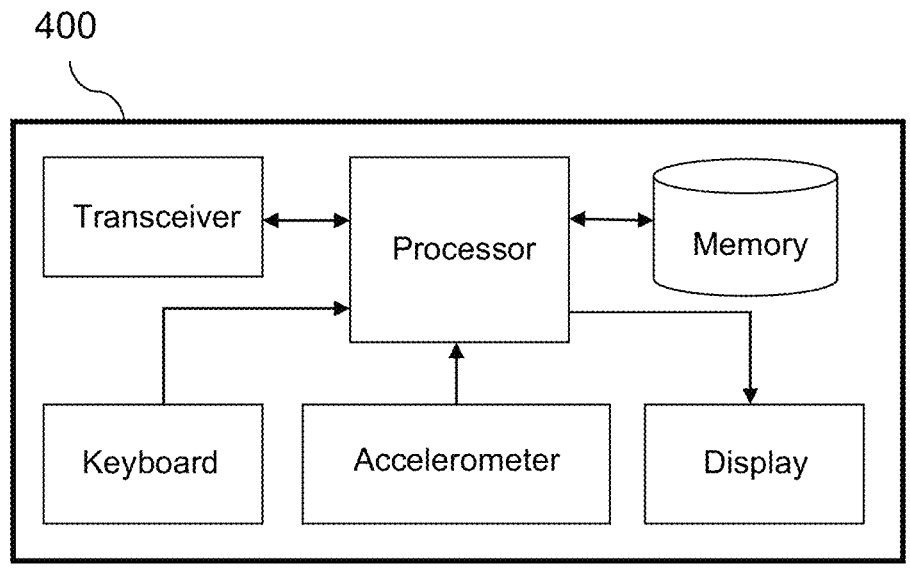
FIG. 31 illustrates a block diagram for a portable computing device for acquiring, processing, and transmitting biometric data in accordance with another embodiment of the present invention.

While different biometric data can be used to determine whether a patient is suffering from COVID-19 (e.g., the presence of a fever, etc.), pulse oximeter data is particularly relevant as the virus very often results in respiratory complications and can therefore be detected by analyzing the patient's blood oxygen saturation percentage (or level) or in conjunction with respiratory rate However, readings from a pulse oximeter are only accurate if the patient is relatively still while the data is being acquired. Thus, it may be necessary for the present invention to determine whether the patient is still (or sufficiently still) while pulse oximeter data is being acquired. This is further necessary if the measurement of respiratory rate is being acquired through deriving a value for this algorithmically from, in this case, the underlying oximetry values. In one embodiment, this is accomplished using the accelerometer within the communication device (see FIG. 31). An accelerometer is an electromechanical device used to measure acceleration forces, which can be static (constant, like gravity) or dynamic (movement or vibrations). Acceleration is the measurement of the change in velocity, or speed divided by time. Typical accelerometers are made up of multiple axes, two to determine most two-dimensional movement with the option of a third for 3D positioning. Most smartphones typically make use of three-axis models. The sensitivity of these devices is quite high as they are intended to measure even very minute shifts in acceleration. The more sensitive the accelerometer, the more easily it can measure acceleration.

By using the accelerometer in the communication device 108 (e.g., smartphone), the application can ensure that the patient is not moving (or sufficiently immobile) while pulse oximeter data (or other vital signs) are being measured. Generally speaking, the less movement, the greater certainty as to the accuracy of the reading (although other factors are known which can also affect the ability to acquire accurate data from the oximeter, such as for example nail polish on a finger nail preventing the light passing through to the recording sensor on an oximeter worn on a finger etc. In such cases the medical staff or an instruction manual given with the device, or an FAQ visible in the application help file etc. will inform the patient of the way to ensure that the device can acquire correct readings). Thus, a predetermined value for movement may be used to ensure that a certain level of accuracy is achieved.

Figure 32:
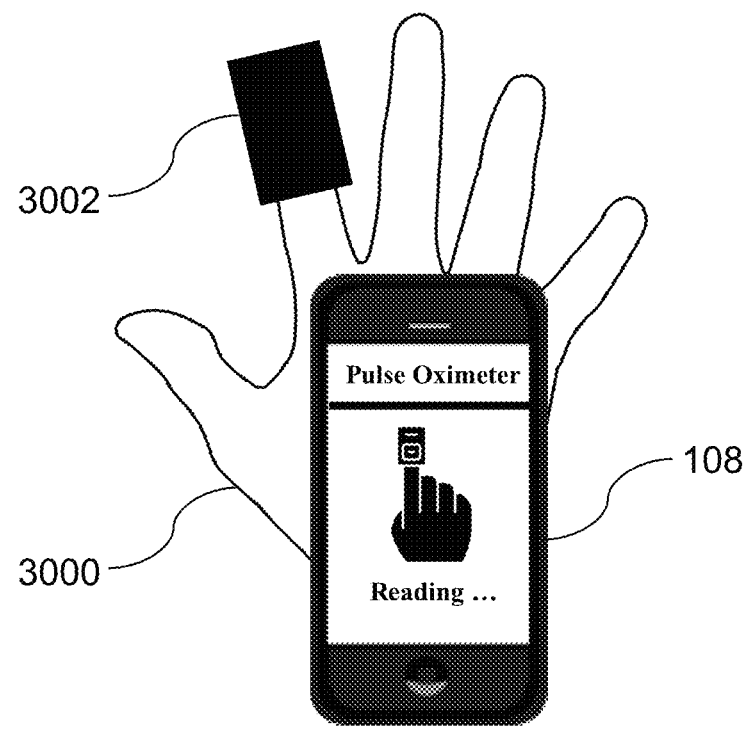
FIG. 32 illustrates one way of ensuring accuracy of biometric data (e.g., pulse oximeter data, etc.) acquired via the mobile computing device, as illustrated in FIG. 31.
Figure 33:
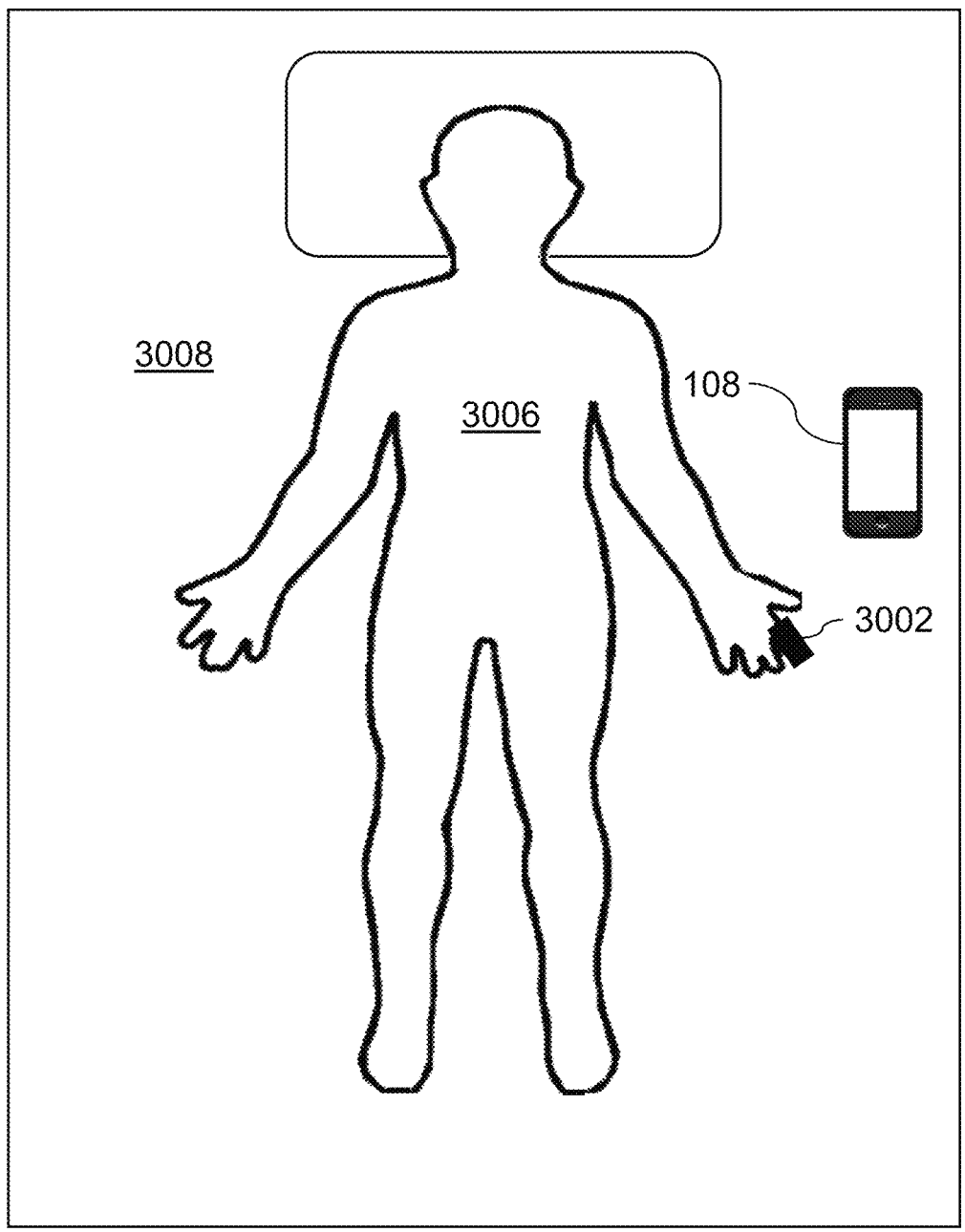
FIG. 33 illustrates a first alternate way of ensuring accuracy of biometric data (e.g., pulse oximeter data, etc.) acquired via the mobile computing device, as illustrated in FIG. 31.

If the patient is holding the communication device 108, as shown in FIG. 32, then the accelerometer (or the like (e.g. gyroscope, etc.)) can be used to measure movement (or the lack thereof) in the patient. In other words, if the patient is moving, then most likely the phone will move as well. This would also be the case if the user were lying on a bed, with the communication device 108 by their side (see FIG. 33); if the patient moved around during acquisition of the biometric data, then the smartphone would register this through the movement in the bed mattress.

Figure 34:
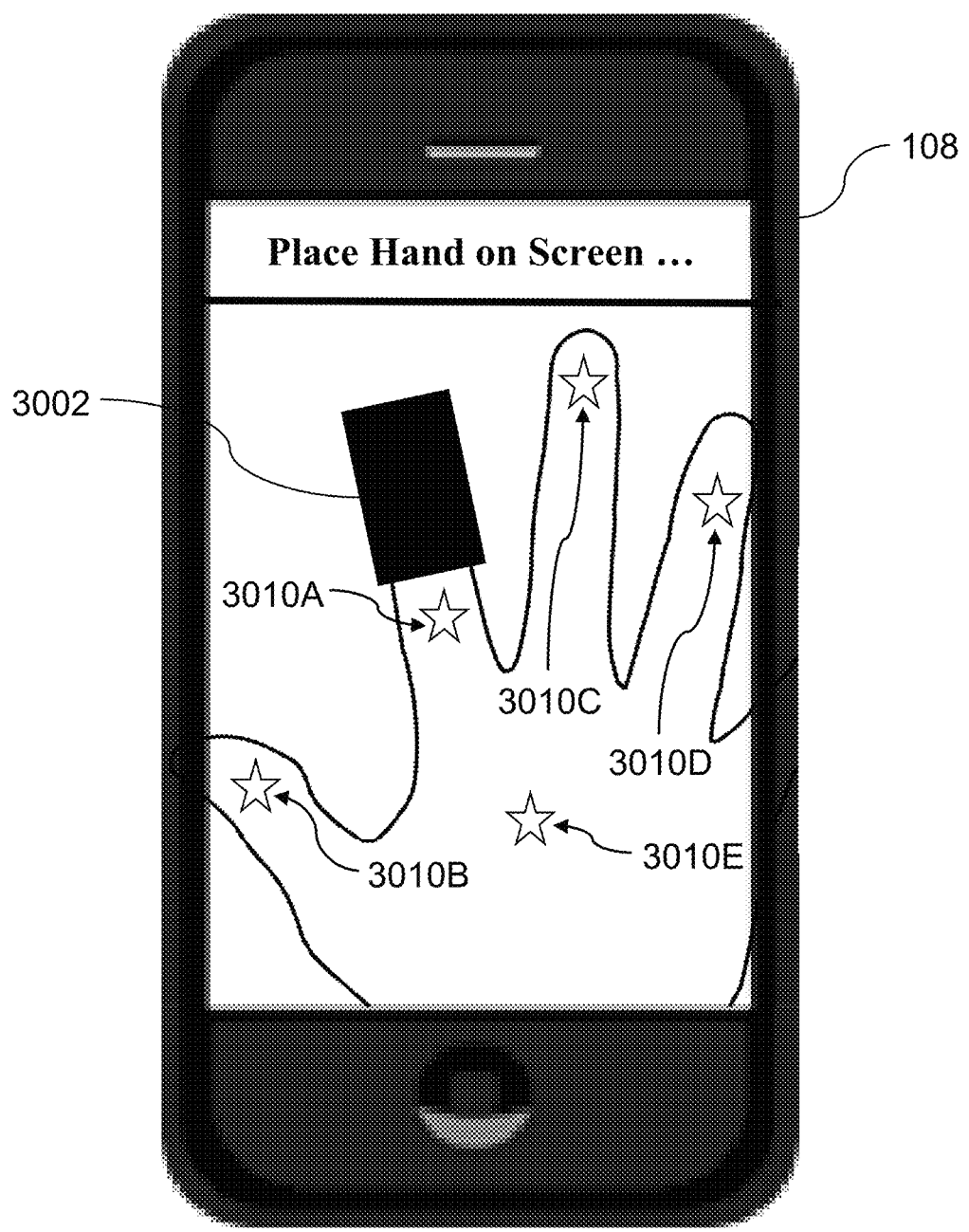
FIG. 34 illustrates a second alternate way of ensuring accuracy of biometric data (e.g., pulse oximeter data, etc.) acquired via the mobile computing device, as illustrated in FIG. 31.

However, if the communication device is on a fixed surface (e.g., a table), then other techniques may be used to ensure that the patient is remaining relatively still. For example, as shown in FIG. 34, the user may be asked to place their hand on the device's touchscreen. The touchscreen (or resistive or capacitive properties thereof) could then be used to ensure that the patient is not moving (or remaining sufficiently still such that no or minimal movement is registered). This may be accomplished by monitoring movement of the pulse oximeter 3002 while in use. Alternatively, the device could measure movement at a location adjacent to the pulse oximeter 3010A (as the pulse oximeter itself, which may be made out of plastic or metal, may not register as a "touch"), of individual fingers (3010B, 3010C, 3010D), and/or the palm 3010E.

It should be appreciated that while a finger pulse oximeter is illustrated in FIGS. 30 and 32-34, the present invention is not so limited, and other pulse oximeters (e.g., incorporated into the smartphone, wristwatch, etc.) are within the spirit and scope of the present invention. It should also be appreciated that the foregoing are merely examples and other methods for determining movement are within the spirit and scope of the present invention. For example, the communication device may also (or alternatively) use its GPS (or location) feature (e.g., triangulation, etc.) to detect movement, use its camera and facial recognition to ensure that the patient is not moving, or merely compare pulse oximeter data over a period of time (e.g., if the pulse oximeter data does not change or fluctuate over time, then it is more likely that the patient is not moving during this period of time). It should also be appreciated that the accelerometer, if used to detect movement, does not have to be in the communication device, and may be located within the pulse oximeter itself or other device in communication with the communication device. Regardless of how the system measures movement, it can use this data to ensure that the data that is being acquired has not been rendered inaccurate through movement of the patient. This is true regardless of what data is being measured and how that data is being used. For example, while pulse oximeter data can be used to diagnose a respiratory infection, it may also be used to diagnose other illnesses or disorders, such as sleep apnea.

Figure 35:
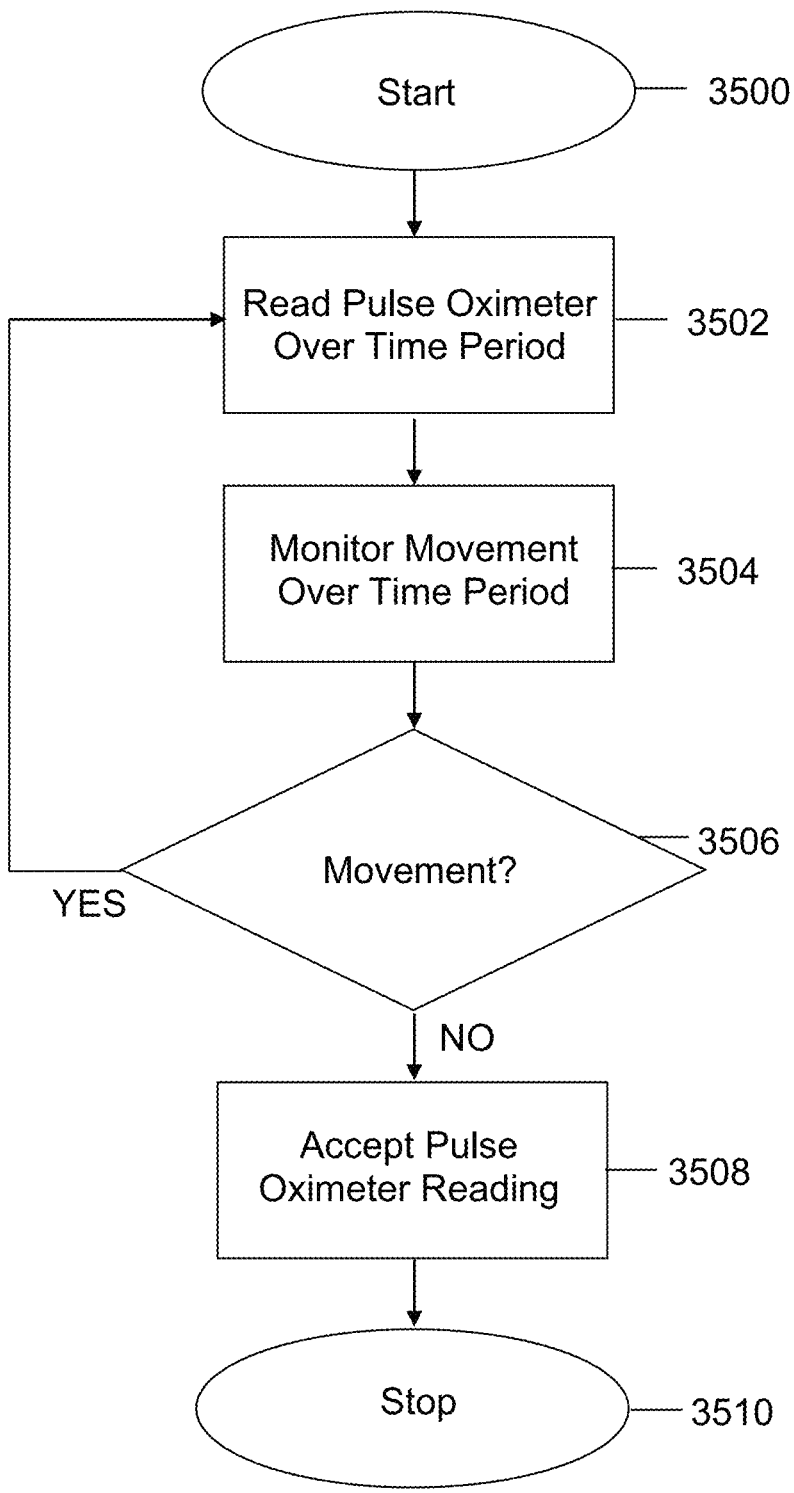
FIG. 35 illustrates a method for ensuring accuracy of acquired biometric data (e.g., pulse oximeter data, etc.) in accordance with one embodiment of the present invention.

A method of using movement data to ensure accuracy is provided in FIG. 35. Starting at step 3500, pulse oximeter data is acquired over a period of time at step 3502. Pulse oximeters generally take readings periodically at regular intervals (a technique known as sampling). By way of example, if the pulse oximeter is configured to sample data at a rate of sixty readings per minute, then it should provide ten readings to the device over a ten second period. At step 3504, the device will measure movement of the patient (as discussed above). A determination will then be made at step 3506 as to whether the patient (or device) is moving, and if so, whether the movement is acceptable. If movement is detected (e.g., above the allowable rate), then pulse oximeter data is reacquired at step 3502. Otherwise, the pulse oximeter readings (or at least one thereof) are considered accurate at step 3508, ending the method at step 3510. It should be appreciated that the present invention is not limited to the foregoing method, and other methods, including fewer, additional, and/or different steps, are within the spirit and scope of the present invention.

Another method for measuring respiratory rate which neither uses an additional device to the oximeter and mobile phone, nor derives a value algorithmically from the vital signs data provided by the oximeter would be for the patient to place the mobile phone on the chest area or thorax, whilst lying supine on their back, and use the accelerometer within the mobile phone to measure within a specified period of time (say a period of a minimum of one thirty second increment) the amount of times the phone was moved up and down, representing one complete breath cycle. See, e.g., FIG. 33, where the phone 108 would be resting on the chest of the user 3006.

In one embodiment, this could be done independently (at another time) to the oximetry measurement, as has already been described. However, in another embodiment, it is possible to combine the movement of the smartphone via the accelerometer readings with the measurement of respiratory rate. In other words, within the mobile phone application, when measuring respiratory rate using this method at the same time as using the oximeter for the other readings, the application would have a setting for measuring respiratory rate and the accelerometer within the smartphone would be regulated to recognize that the phone was now in RR measurement mode from the distinctive movement pattern of the patient's breathing cycle (inhale/exhale). In this embodiment it would be preferable to combine the measurement of oximeter readings, whereby the value for RR derived algorithmically from the oximeter readings could be cross-checked against the readings for RR from the accelerometer on the smartphone. In this case, it would again be necessary for the patient to remain relatively still during the data acquisition and the accelerometer would be able to recognize if movement of the smartphone placed on the patient's chest area or thorax corresponded to the relative regularity of breathing/respiratory cycle, or instead a non-typical movement signal suggesting instead a more sudden, less typical movement of the smartphone movement of the part of the body to which the oximeter is attached.

In other words, an acceptable level of movement (e.g., to detect breathing) would be allowed, whereas an unacceptable level of movement (e.g., breathing too deep, etc.) would require the user to start the RR/oximeter reading again, this time while moving less. Preferably there would be a predetermined level of movement that would be acceptable. Alternatively, the oximeter readings would be evaluated to determine whether additional readings were necessary.

Regardless of the embodiment, the concern that a monitored party would not wish to be permanently monitored (e.g., a senior citizen not wanting to have their every move and action continuously videoed) could be mitigated by the incorporation of various additional features. In one embodiment, the video would be permanently recording in a loop system which uses a reserved memory space, recording for a predetermined time period, and then, automatically erasing the video, where n represents the selected minutes in the loop and E is the event which prevents the recorded loop of n minutes being erased, and triggers both the real time transmission of the visible state or actions of the monitored person to the monitoring party, as well as the ability to rewind, in order for the monitoring party to be able to review the physical manifestation leading up to E. The trigger mechanism for E could be, for example, the occurrence of biometric data outside the predefined range, or the notification of another anomaly such as a fall alert, activated by movement or location sensors such as a gyroscope, accelerometer or magnetometer within the health band device worn by, say the senior citizen, or on their mobile phone or other networked motion-sensing device in their proximity. The monitoring party would be able not only to view the physical state of the monitored party after E, whilst getting a simultaneous read-out of their relevant biometric data, but also to review the events and biometric data immediately leading up to the event trigger notification. Alternatively, it could be further calibrated so that although video is recorded, as before, in the n loop, no video from the n loop will actually be transmitted to a monitoring party until the occurrence of E. The advantages of this system include the respect of the privacy of the individual, where only the critical event and the time preceding the event would be available to a third party, resulting also in a desired optimization of both the necessary transmission bandwidth and the data storage requirements. It should be appreciated that the foregoing system could also be configured such that the E notification for remote senior, infant or patient monitoring is further adapted to include facial tracking and/or expression recognition features.

Privacy could be further improved for the user if their video data and biometric data are stored by themselves, on their own device, or on their own external, or own secure third-party "cloud" storage, but with the index metadata of the source material, which enables the sequencing, extrapolation, searching and general processing of the source data, remaining at a central server, such as, in the case of medical records for example, at a doctor's office or other healthcare facility. Such a system would enable the monitoring party to have access to the video and other data at the time of consultation, but with the video etc. remaining in the possession of the subject. A further advantage of separating the hosting of the storage of the video and biometric source data from the treatment of the data, beyond enhancing the user's privacy and their data security, is that by virtue of its storage locally with the subject, not having to upload it to the computational server results both in reduced cost and increased efficiency of storage and data bandwidth. This would be of benefit also where such kind of remote upload of tests for review by qualified medical staff at a different location from the subject are occurring in areas of lower-bandwidth network coverage. A choice can also be made to lower the frame rate of the video material, provided that this is made consistent with sampling rate to confirm the correct time stamp, as previously described.

It should be appreciated that with information being stored at the central server (or the host device), various techniques known in the art can be implemented to secure the information, and prevent unauthorized individuals or entities from accessing the information. Thus, for example, a user may be provided (or allowed to create) a user name, password, and/or any other identifying (or authenticating) information (e.g., a user biometric, a key fob, etc.), and the host device may be configured to use the identifying (or authenticating) information to grant access to the information (or a portion thereof). Similar security procedures can be implemented for third parties, such as medical providers, insurance companies, etc., to ensure that the information is only accessible by authorized individuals or entities. In certain embodiments, the authentication may allow access to all the stored data, or to only a portion of the stored data (e.g., a user authentication may allow access to personal information as well as stored video and/or biometric data, whereas a third party authentication may only allow access to stored video and/or biometric data). In other embodiments, the authentication is used to determine what services are available to an individual or entity logging into the host device, or the website. For example, visitors to the website (or non-subscribers) may only be able to synchronize video/audio data to biometric data and/or perform rudimentary searching or other processing, whereas a subscriber may be able to synchronize video/audio data to biometric data and/or perform more detailed searching or other processing (e.g., to create a highlight reel, etc.).

It should further be appreciated that while there are advantages to keeping just the index metadata at the central server in the interests of storage and data upload efficiency as well as so providing a common platform for the interoperability of the different data types and storing the video and/or audio data on the user's own device (e.g., iCloud™, DropBox™, OneDrive™, etc.), the present invention is not so limited. Thus, in certain embodiments, where feasible, it may be beneficial to (1) store data (e.g., video, audio, biometric data, and metadata) on the user's device (e.g., allowing the user device to operate independent of the host device), (2) store data (e.g., video, audio, biometric data, and metadata) on the central server (e.g., host device) (e.g., allowing the user to access the data from any network-enabled device), or (3) store a first portion (e.g., video and audio data) on the user's device and store a second portion (e.g., biometric data and metadata) on the central server (e.g., host device) (e.g., allowing the user to only view the synchronized video/audio/biometric data when the user device is in communication with the host device, allowing the user to only search the biometric data (e.g., to create a "highlight reel") or rank the biometric data (to identify and/or list data chronologically, magnitude (highest to lowest), magnitude (lowest to highest), best reviewed, worst reviewed, most viewed, least viewed, etc.) when the user device is in communication with the host device, etc.).

In another embodiment of the present invention, the functionality of the system is further (or alternatively) limited by the software operating on the user device and/or the host device. For example, the software operating on the user device may allow the user to play the video and/or audio data, but not to synchronize the video and/or audio data to the biometric data. This may be because the central server is used to store data critical to synchronization (time-stamp index, metadata, biometric data, sample rate, etc.) and/or software operating on the host device is necessary for synchronization. By way of another example, the software operating on the user device may allow the user to play the video and/or audio data, either alone or synchronized with the biometric data, but may not allow the user device (or may limit the user device's ability) to search or otherwise extrapolate from, or process the biometric data to identify relevant portions (e.g., which may be used to create a "highlight reel" of the synchronized video/audio/biometric data) or to rank the biometric and/or video data. This may be because the central server is used to store data critical to search and/or rank the biometric data (biometric data, biometric metadata, etc.), and/or software necessary for searching (or performing advanced searching of) and/or ranking (or performing advanced ranking of) the biometric data.

In any or all of the above embodiments, the system could be further adapted to include password or other forms of authentication to enable secured access (or deny unauthorized access) to the data in either of one or both directions, such that the user requires permission to access the host, or the host to access the user's data. Where interaction between the user and the monitoring party or host is occurring in real time such as in a secure video consult between patient and their medical practitioner or other medical staff, data could be exchanged and viewed through the establishment of a Virtual Private Network (VPN). The actual data (biometric, video, metadata index, etc.) can alternatively or further be encrypted both at the data source, for example at the individual's storage, whether local or cloud-based, and/or at the monitoring reviewing party, for example at patient records at the medical facility, or at the host administration level.

In the context of very young infant monitoring, a critical and often unexplained problem is Sudden Infant Death Syndrome (SIDS). Whilst the incidences of SIDS are often unexplained, various devices attempt to prevent its occurrence. However, by combining the elements of the current system to include sensor devices in or near the baby's crib to measure relevant biometric data including heart rate, sleep pattern, breath analyzer, and other measures such as ambient temperature, together with a recording device to capture movement, audible breathing, or lack thereof (i.e., silence) over a predefined period of time, the various parameters could be set in conjunction with the time-stamped video record, by the parent, medical or other monitoring party, to provide a more comprehensive alert, to initiate a more timely action or intervention by the user, or indeed to decide that no action response would in fact be necessary. Additionally, in the case, for example, of a crib monitoring situation, the system could be so configured to develop from previous observation, with or without input from a monitoring party, a learning algorithm to help in discerning what is "normal," what is false positive, or what might constitute an anomaly, and therefore a call to action. In the furthermore complex context such as neo-natal monitoring other biometric data could include EEG, EOC and EMG sensors.

The host application could also be configured to play video data that has been synchronized to biometric data, or search for the existence of certain biometric data. For example, as previously discussed, by video recording with sound a person sleeping, and synchronizing the recording with biometric data (e.g., sleep patterns, brain activity, snoring, breathing patterns, etc.), the biometric data can be searched to identify where certain measures such as sound levels, as measured for example in decibels, or periods of silences, exceed or drop below a threshold value, allowing the doctor, nurse, or medical technician to view the corresponding video portion without having to watch the entire video of the person sleeping.

Figure 6:
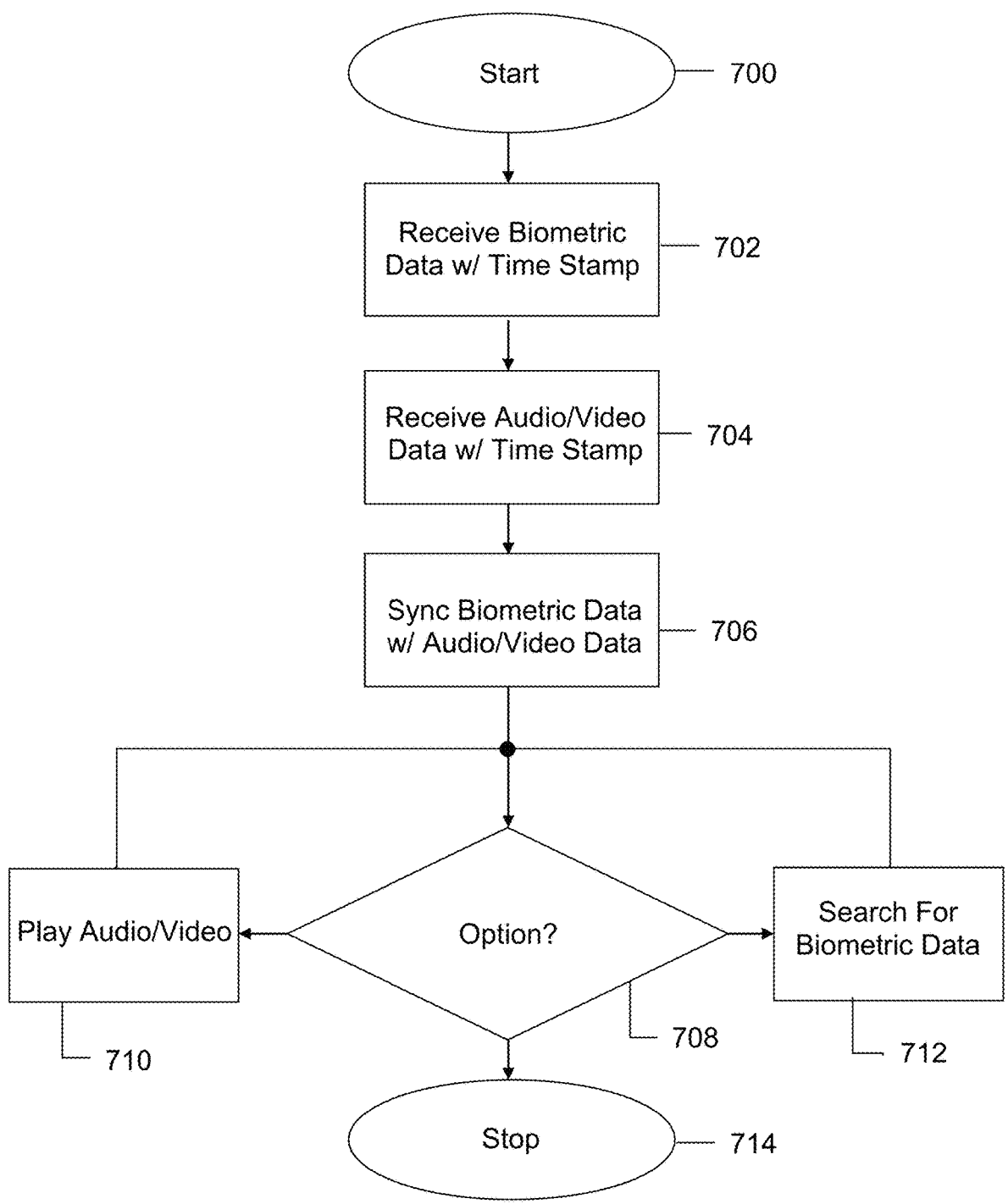
FIG. 6 illustrates a method for synchronizing video data with biometric data, operating the video data, and searching the biometric data, in accordance with one embodiment of the present invention.

Such a method is shown in FIG. 6, starting at step 700, where biometric data and time stamp data (e.g., start time, sample rate) is received (or linked) at step 702. Audio/video data and time stamp data (e.g., start time, etc.) is then received (or linked) at step 704. The time stamp data (from steps 702 and 704) is then used to synchronize the biometric data with the audio/video data. The user is then allowed to operate the audio/video at step 708. If the user selects play, then the audio/video is played at step 710. If the user selects search, then the user is allowed to search the biometric data at step 712. Finally, if the user selects stop, then the video is stopped at step 714.

It should be appreciated that the present invention is not limited to the steps shown in FIG. 6. For example, a method that allows a user to search for biometric data that meets at least one condition, play the corresponding portion of the video (or a portion just before the condition), and stop the video from playing after the biometric data no longer meets the at least one condition (or just after the biometric data non longer meets the condition) is within the spirit and scope of the present invention. By way of another example, if the method involves interacting between the user device and the host device to synchronize the video/audio data and the biometric data and/or search the biometric data, then the method may further involve the steps of uploading the biometric data and/or metadata to the host device (e.g., in this embodiment the video/audio data may be stored on the user device), and using the biometric data and/or metadata to create a time-stamp index for synchronization and/or to search the biometric data for relevant or meaningful data (e.g., data that exceeds a threshold, etc.). By way of yet another example, the method may not require step 706 if the audio/video data and the biometric data are played together (synchronized) in real-time, or at the time the data is being played (e.g., at step 710).

Figure 8:
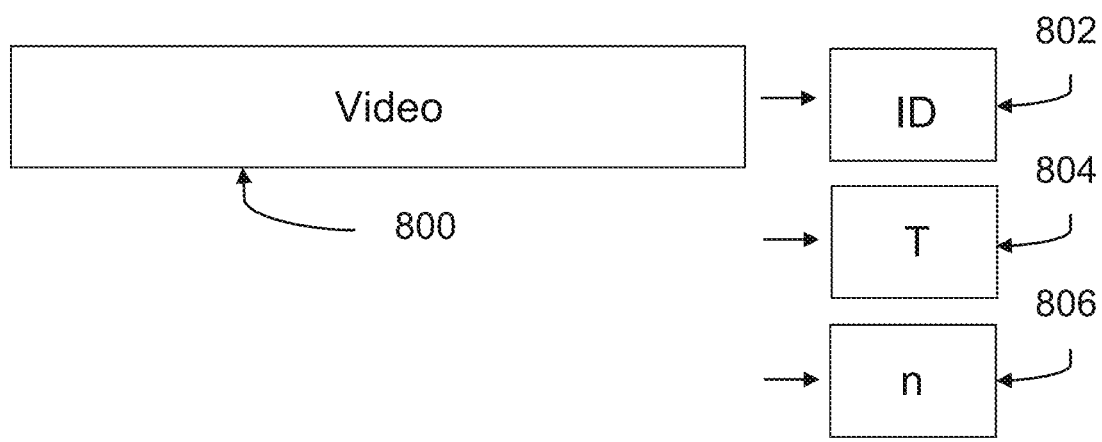
FIG. 8 illustrates exemplary video data, which is preferably linked to an identifier (ID), a start time (T), and a finish time or duration (n)
Figure 9:
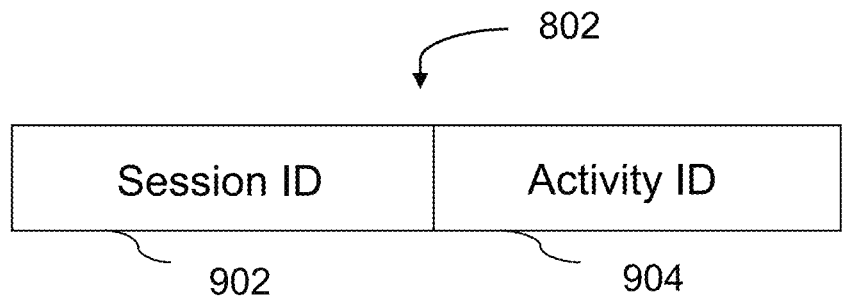
FIG. 9 illustrates an exemplary identifier (ID), comprising a session identifier and an activity identifier.

In one embodiment of the present invention, as shown in FIG. 8, the video data 800, which may also include audio data, starts at a time "T" and continues for a duration of "n." The video data is preferably stored in memory (locally and/or remotely) and linked to other data, such as an identifier 802, start time 804, and duration 806. Such data ties the video data to at least a particular session, a particular start time, and identifies the duration of the video included therein. In one embodiment of the present invention, each session can include different activities. For example, a trip to a destination in Berlin, or following a specific itinerary on a particular day (session) may involve a bike ride through the city (first activity) and a walk through a park (second activity). Thus, as shown in FIG. 9, the identifier 802 may include both a session identifier 902, uniquely identifying the session via a globally unique identifier (GUID), and an activity identifier 904, uniquely identifying the activity via a globally unique identifier (GUID), where the session/activity relationship is that of a parent/child.

Figure 10:
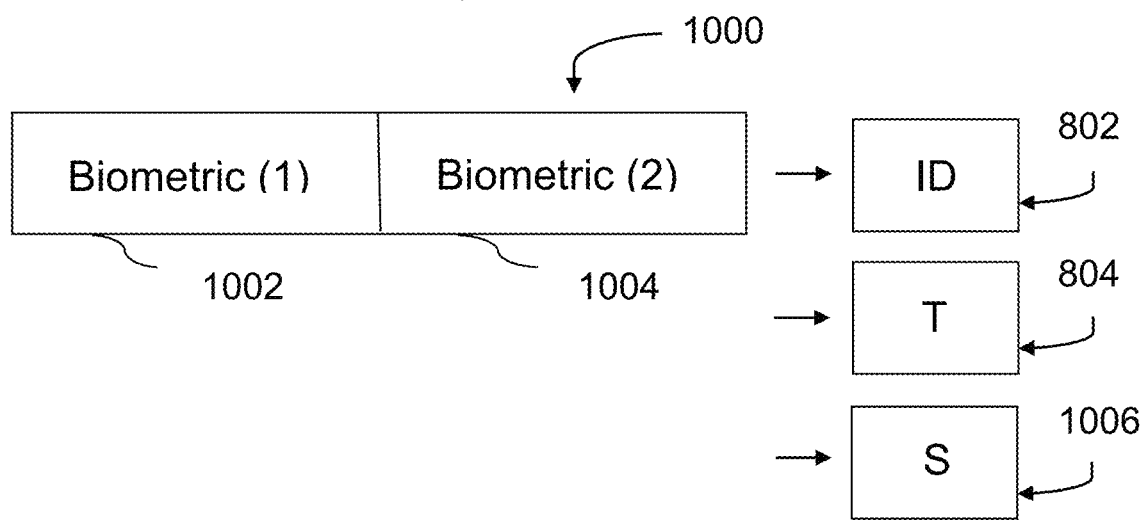
FIG. 10 illustrates exemplary biometric data, which is preferably linked to an identifier (ID), a start time (T), and a sample rate (S)
Figure 11:
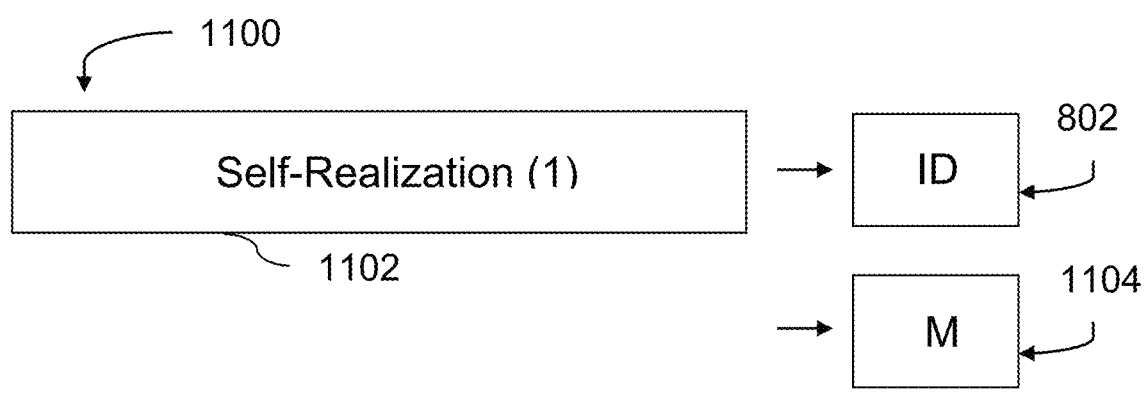
FIG. 11 illustrates exemplary self-realization data, which is preferably linked to an identifier (ID) and a time (m)

In one embodiment of the present invention, as shown in FIG. 10, the biometric data 1000 is stored in memory and linked to the identifier 802 and a sample rate "m" 1104. This allows the biometric data to be linked to video data upon playback. For example, if identifier 802 is one, start time 804 is 1:00 PM, video duration is one minute, and the sample rate 1104 is 30 spm, then the playing of the video at 2:00 PM would result in the first biometric value (biometric (1)) to be displayed (e.g., below the video, over the video, etc.) at 2:00 PM, the second biometric value (biometric (2)) to be displayed (e.g., below the video, over the video, etc.) two seconds later, and so on until the video ends at 2:01 PM. While self-realization data can be stored like biometric data (e.g., linked to a sample rate), if such data is only received periodically, it may be more advantageous to store this data 110 as shown in FIG. 11, i.e., linked to the identifier 802 and a time-stamp 1104, where "m" is either the time that the self-realization data 1100 was received or an offset between this time and the start time 804 (e.g., ten minutes and four seconds after the start time, etc.).

Figure 14:
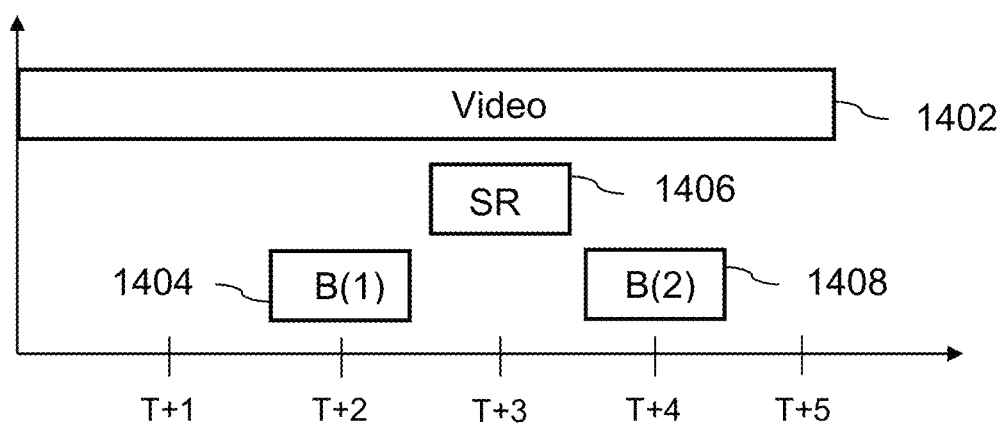
FIG. 14 illustrates an example of how a start time and data related thereto (e.g., sample rate, etc.) can be used to synchronized biometric data and self-realization data to video data.

This can be seen, for example, in FIG. 14, where video data starts at time T, biometric data is sampled every two seconds (30 spm), and self-realization data is received at time T+3 (or three units past the start time). While the video 1402 is playing, a first biometric value 1404 is displayed at time T+1, first self-realization data 1406 is displayed at time T+2, and a second biometric value 1406 is displayed at time T+4. By storing data in this fashion, both video and non-video data can be stored separately from one another and synchronized in real-time, or at the time the video is being played. It should be appreciated that while separate storage of data may be advantageous for devices having minimal memory and/or processing power, the client platform may be configured to create new video data, or data that includes both video and non-video data displayed synchronously. Such a feature may advantageous in creating a highlight reel, which can then be shared using social media websites, such as Facebook™ or Youtube™, and played using standard playback software, such as Quicktime™. As discussed in greater detail below, a highlight reel may include various portions (or clips) of video data (e.g., when certain activity takes place, etc.) along with corresponding biometric data.

Figure 12:
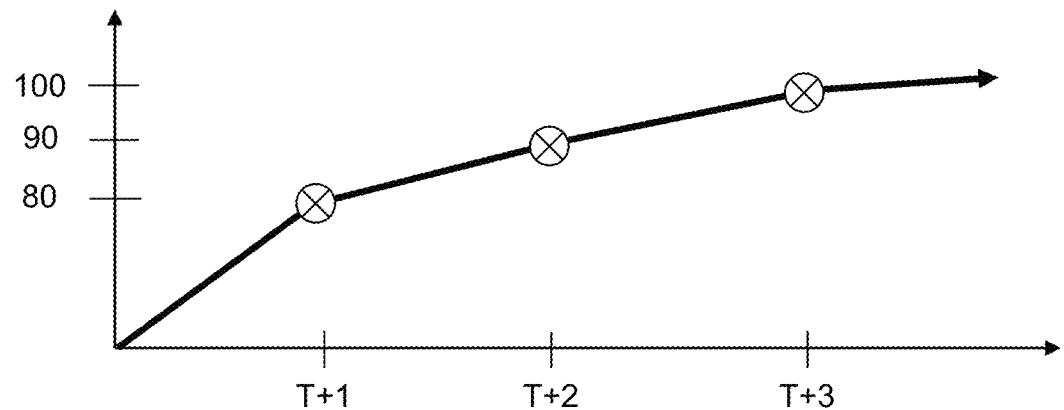
FIG. 12 illustrates how sampled biometric data points can be used to extrapolate other biometric data point in accordance with one embodiment of the present invention.
Figure 13:
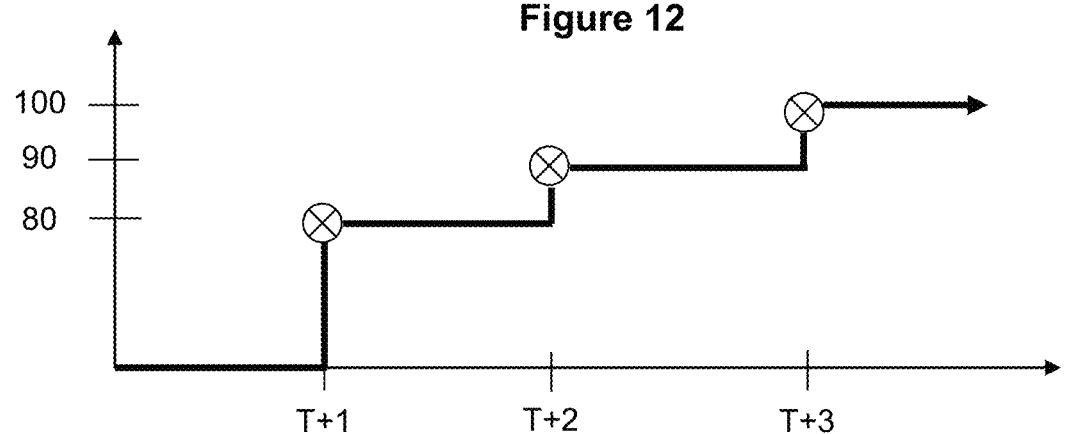
FIG. 13 illustrates how sampled biometric data points can be used to extrapolate other biometric data points in accordance with another embodiment of the present invention.

When sampled data is subsequently displayed, the client platform can be configured to display this data using certain extrapolation techniques. For example, in one embodiment of the present invention, as shown in FIG. 12, where a first biometric value 1202 is displayed at T+1, a second biometric value 1204 is displayed at T+2, and a third biometric value 1206 is displayed at T+3, biometric data can be displayed at non-sampled times using known extrapolation techniques, including linear and non-linear interpolation and all other extrapolation and/or interpolation techniques generally known to those skilled in the art. In another embodiment of the present invention, as shown in FIG. 13, the first biometric value 1202 remains on the display until the second biometric value 1204 is displayed, the second biometric value 1204 remains on the display until the third biometric value 1206 is displayed, and so on.

With respect to linking data to an identifier, which may be linked to other data (e.g., start time, sample rate, etc.), if the data is received in real-time, the data can be linked to the identifier(s) for the current session (and/or activity). However, when data is received after the fact (e.g., after a session has ended), there are several ways in which the data can be linked to a particular session and/or activity (or identifier(s) associated therewith). The data can be manually linked (e.g., by the user) or automatically linked via the application. With respect to the latter, this can be accomplished, for example, by comparing the duration of the received data (e.g., the video length) with the duration of the session and/or activity, by assuming that the received data is related to the most recent session and/or activity, or by analyzing data included within the received data. For example, in one embodiment, data included with the received data (e.g., metadata) may identify a time and/or location associated with the data, which can then be used to link the received data to the session and/or activity. In another embodiment, the computing device could display or play data (e.g., a barcode, such as a QR code, a sound, such as a repeating sequence of notes, etc.) that identifies the session and/or activity. An external video/audio recorder could record the identifying data (as displayed or played by the computing device) along with (e.g., before, after, or during) the user and/or his/her surroundings. The application could then search the video/audio data for identifying data and use this data to link the video/audio data to a session and/or activity. The identifying portion of the video/audio data could then be deleted by the application if desired. In an alternate embodiment, a barcode (e.g., a QR code) could be printed on a physical device (e.g., a medical testing module, which may allow communication of medical data over a network (e.g., via a smart phone)) and used (as previously described) to synchronize video of the user using the device to data provided by the device. In the case of a medical testing module, the barcode printed on the module could be used to synchronize video of the testing to the test result provided by the module. In yet another embodiment, both the computing device and the external video/audio recorder are used to record video and/or audio of the user (e.g., the user stating "begin Berlin biking session," etc.) and to use the user-provided data to link the video/audio data to a session and/or activity. For example, the computing device may be configured to link the user-provided data with a particular session and/or activity (e.g., one that is started, one that is about to start, one that just ended, etc.), and to use the user-provided data in the video/audio data to link the video/audio data to the particular session and/or activity.

In one embodiment of the present invention, the client platform (or application) is configured to operate on a smart phone or a tablet. The platform (either alone or together with software operating on the host device) may be configured to create a session, receive video and non-video data during the session, and playback video data together (synchronized) with non-video data. The platform may also allow a user to search for a session, search for certain video and/or non-video events, and/or create a highlight reel. FIGS. 15-29 show exemplary screen shots of such a platform.

Figure 15:
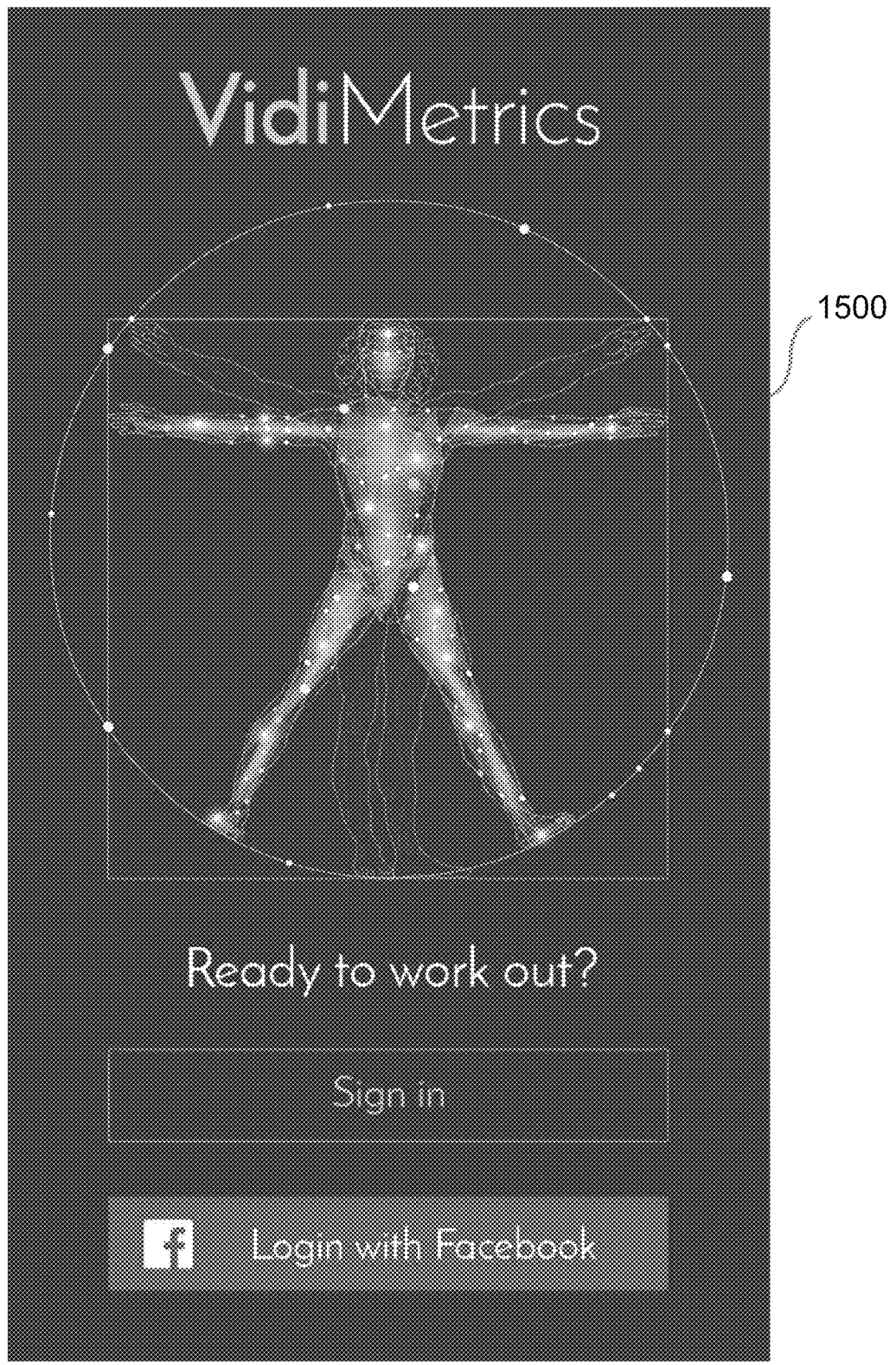
FIG. 15 depicts an exemplary "sign in" screen shot for an application that allows a user to capture at least video and biometric data of the user performing an athletic event (e.g., bike riding, etc.) and to display the video data together (or in synchronization) with the biometric data.

For example, FIG. 15 shows an exemplary "sign in" screen 1500, allowing a user to sign into the application and have access to application-related, user-specific data, as stored on the computing device and/or the host computing device. The login may involve a user ID and password unique to the application, the company cloud, or a social service website, such as Facebook™.

Figure 16:
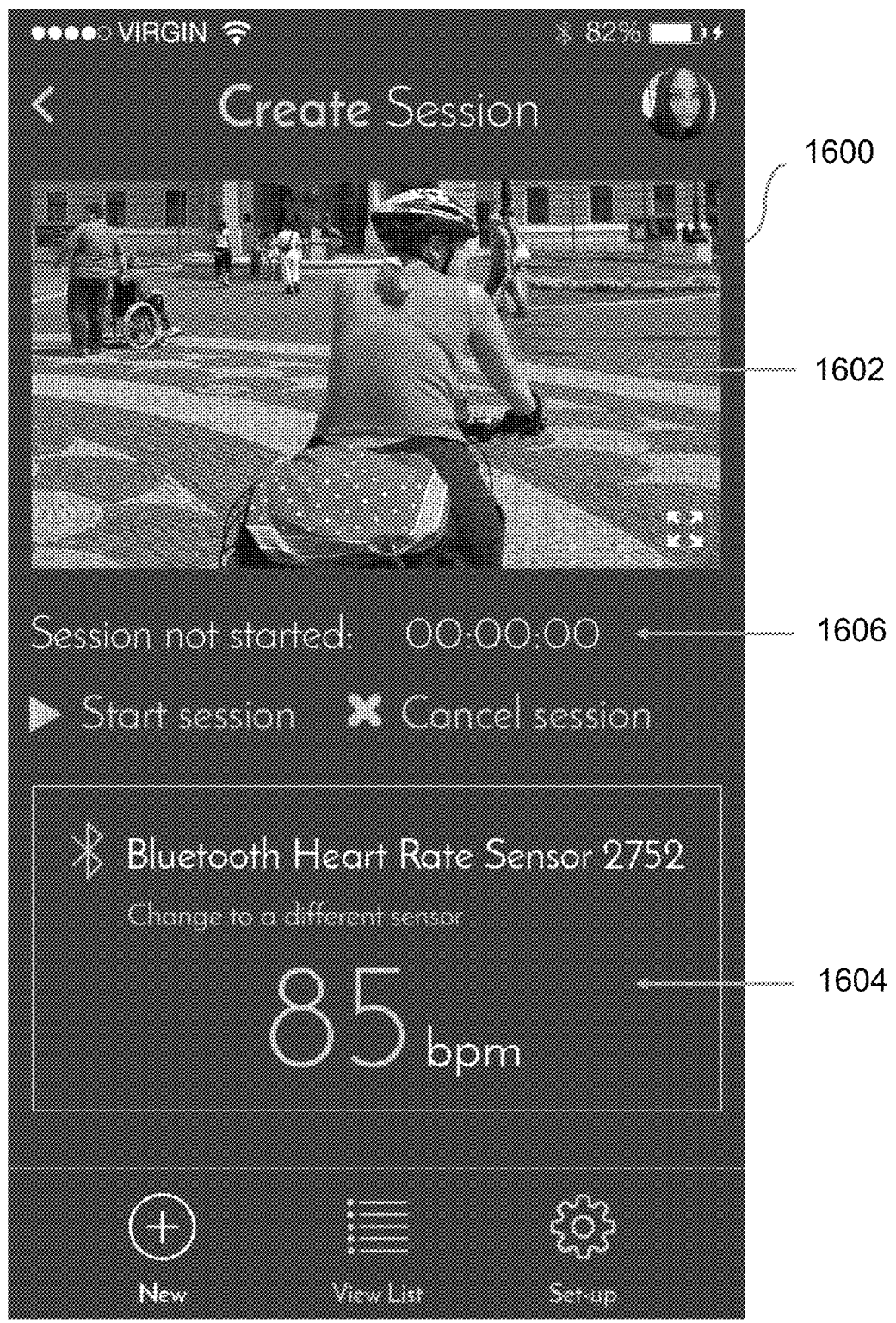
FIG. 16 depict an exemplary "create session" screen shot for the application depicted in FIG. 15, allowing the user to create a new session.

Once the user is signed in, the user may be allowed to create a session via an exemplary "create session" screen 1600, as shown in FIG. 16. In creating a session, the user may be allowed to select a camera (e.g., internal to the computing device, external to the computing device (e.g., accessible via the Internet, connected to the computing device via a wired or wireless connection), etc.) that will be providing video data. Once a camera is selected, video data 1602 from the camera may be displayed on the screen. The user may also be allowed to select a biometric device (e.g., internal to the computing device, external to the computing device (e.g., accessible via the Internet, connected to the computing device via a wired or wireless connection), etc.) that will be providing biometric data. Once a biometric device is selected, biometric data 1604 from the biometric device may be displayed on the screen. The user can then start the session by clicking the "start session" button 1608. While the selection process is preferably performed before the session is started, the user may defer selection of the camera and/or biometric device until after the session is over. This allows the application to receive data that is not available in real-time, or is being provided by a device that is not yet connected to the computing device (e.g., an external camera that will be plugged into the computing device once the session is over).

It should be appreciated that in a preferred embodiment of the present invention, clicking the "start session" button 1608 not only starts a timer 1606 that indicates a current length of the session, but it triggers a start time that is stored in memory and linked to a globally unique identifier (GUID) for the session. By linking the video and biometric data to the GUID, and linking the GUID to the start time, the video and biometric data is also (by definition) linked to the start time. Other data, such as sample rate, can also be linked to the biometric data, either by linking the data to the biometric data, or linking the data to the GUID, which is in turn linked to the biometric data.

Figures 17, 18:
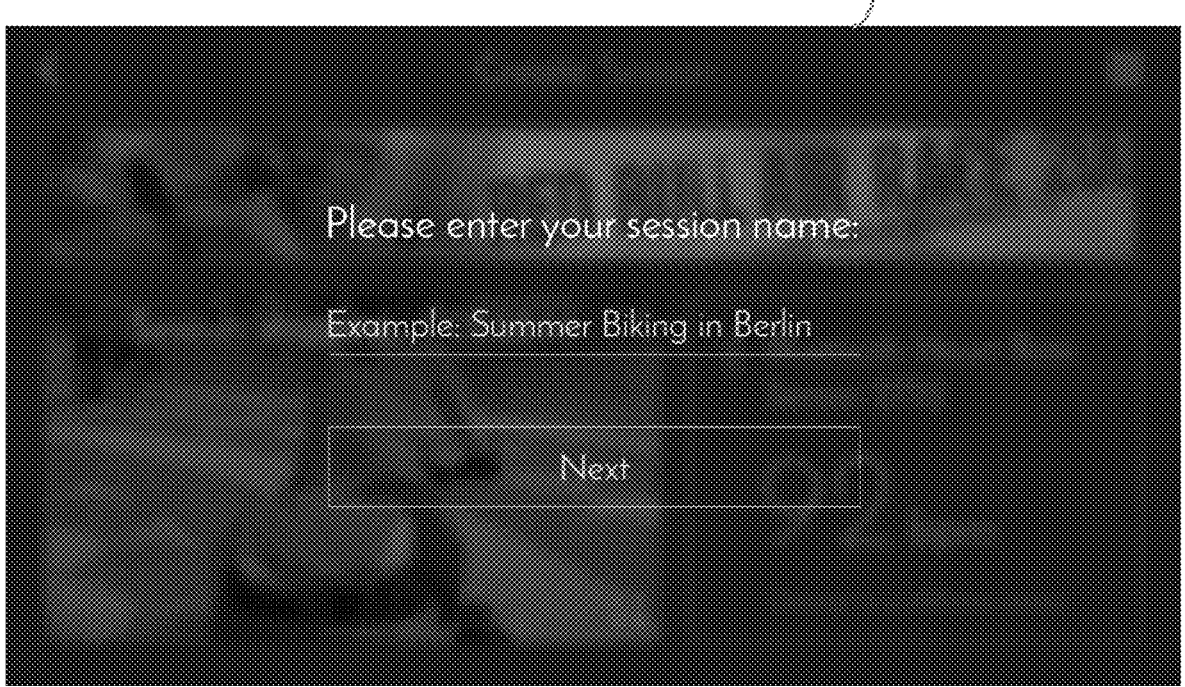
FIG. 17 depicts an exemplary "session name" screen shot for the application depicted in FIG. 15, allowing the user to enter a name for the session.
FIG. 18 depicts an exemplary "session description" screen shot for the application depicted in FIG. 15, allowing the user to enter a description for the session.

Either before the session is started, or after the session is over, the user may be allowed to enter a session name via an exemplary "session name" screen 1700, as shown in FIG. 17. Similarly, the user may also be allowed to enter a session description via an exemplary "session description" screen 1800, as shown in FIG. 18.

FIG. 19 shows an exemplary "session started" screen 1900, which is a screen that the user might see while the session is running. On this screen, the user may see the video data 1902 (if provided in real-time), the biometric data 1904 (if provided in real-time), and the current running time of the session 1906. If the user wishes to pause the session, the user can press the "pause session" button 1908, or if the user wishes to stop the session, the user can press the "stop session" button (not shown). By pressing the "stop session" button (not shown), the session is ended, and a stop time is stored in memory and linked to the session GUID. Alternatively, by pressing the "pause session" button 1908, a pause time (first pause time) is stored in memory and linked to the session GUID. Once paused, the session can then be resumed (e.g., by pressing the "resume session" button, not shown), which will result in a resume time (first resume time) to be stored in memory and linked to the session GUID. Regardless of whether a session is started and stopped (i.e., resulting in a single continuous video), or started, paused (any number of times), resumed (any number of times), and stopped (i.e., resulting in a plurality of video clips), for each start/pause time stored in memory, there should be a corresponding stop/resume time stored in memory.

Once a session has been stopped, it can be reviewed via an exemplary "review session" screen 2000, as shown in FIG. 20. In its simplest form, the review screen may playback video data linked to the session (e.g., either a single continuous video if the session does not include at least one pause/resume, multiple video clips played one after another if the session includes at least one pause/resume, or multiple video clips played together if the multiple video clips are related to one another (e.g., two videos (e.g., from different vantage points) of the user performing a particular activity, a first video of the user performing a particular activity while viewing a second video, such as a training video). If the user wants to see non-video data displayed along with the video data, the user can press the "show graph options" button 2022. By pressing this button, the user is presented with an exemplary "graph display option" screen 2100, as shown in FIG. 21. Here, the user can select data that he/she would like to see along with the video data, such as biometric data (e.g., heart rate, heart rate variance, user speed, etc.), environmental data (e.g., temperature, altitude, GPS, etc.), or self-realization data (e.g., how the user felt during the session). FIG. 22 shows an exemplary "review session" screen 2000 that includes both video data 2202 and biometric data, which may be shown in graph form 2204 or written form 2206. If more than one individual can be seen in the video, the application may be configured to show biometric data on each individual, either at one time, or as selected by the user (e.g., allowing the user to view biometric data on a first individual by selecting the first individual, allowing the user to view biometric data on a second individual by selecting the second individual, etc.).

Figures 23, 24:
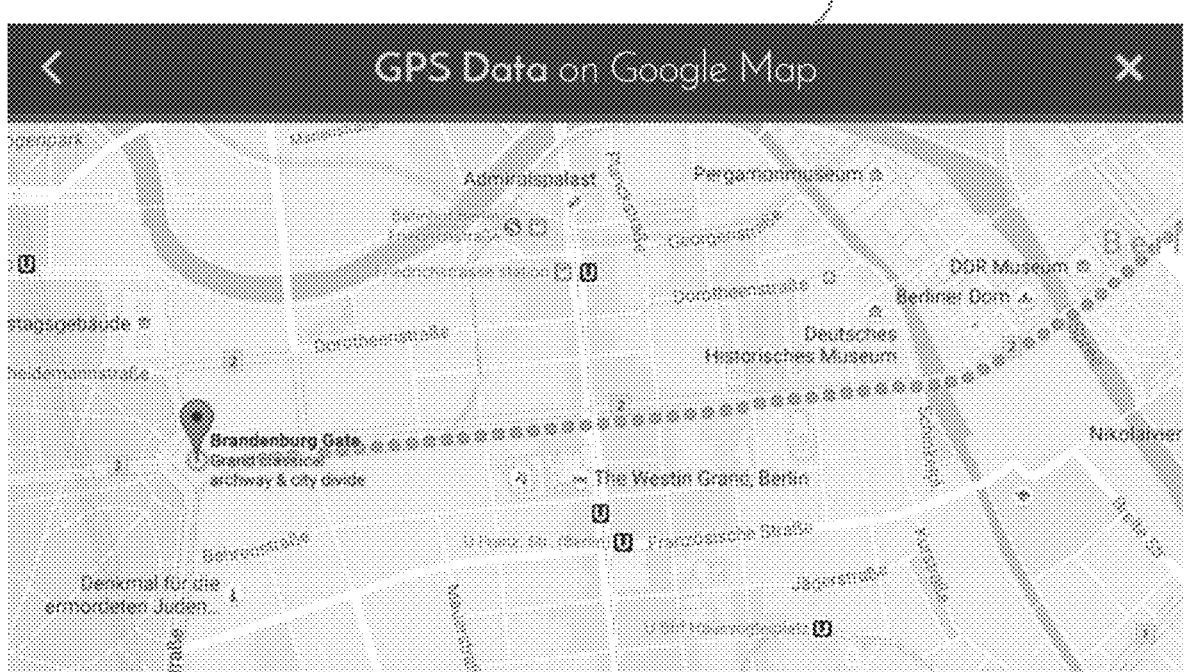
FIG. 23 depicts an exemplary "map" screen shot for the application depicted in FIG. 15, showing GPS data displayed on a Google map.
FIG. 24 depicts an exemplary "summary" screen shot for the application depicted in FIG. 15, showing a summary of the session.

FIG. 23 shows an exemplary "map" screen 2300, which may be used to show GPS data to the user. Alternatively, GPS data can be presented together with the video data (e.g., below the video data, over the video data, etc.). An exemplary "summary" screen 2400 of the session may also be presented to the user (see FIG. 24), displaying session information such as session name, session description, various metrics, etc.

Figure 27:
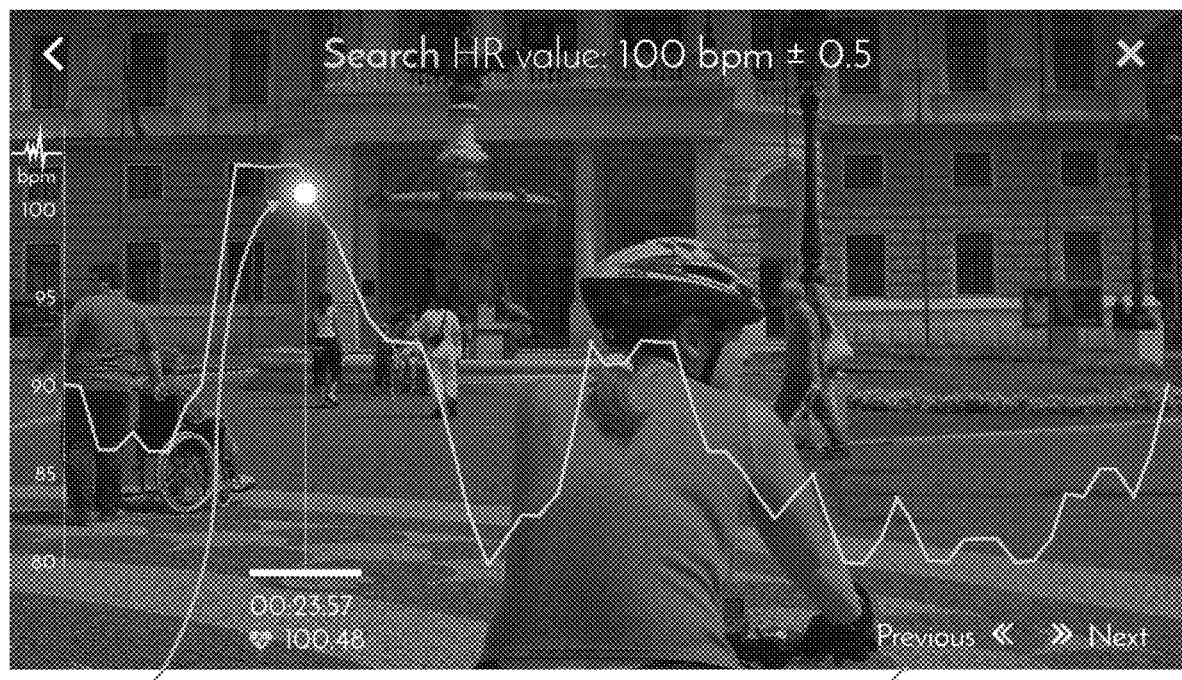
FIG. 27 depicts an exemplary "second result" screen shot for the application depicted in FIG. 15, showing a second result for the biometric event shown in FIG. 25, together with corresponding video.

By storing video and non-video data separately, the data can easily be searched. For example, FIG. 25 shows an exemplary "biometric search" screen 2500, where a user can search for a particular biometric value or range (i.e., a biometric event). By way of example, the user may want to jump to a point in the session where their heart rate is between 95 and 105 beats-per-minute (bpm). FIG. 26 shows an exemplary "first result" screen 2600 where the user's heart rate is at 100.46 bmp twenty minutes and forty-two seconds into the session (see, e.g., 2608). FIG. 27 shows an exemplary "second result" screen 2700 where the user's heart rate is at 100.48 bmp twenty-three minutes and forty-eight seconds into the session (see, e.g., 2708). It should be appreciated that other events can be searched for in a session, including video events and self-realization events.

Figure 28:
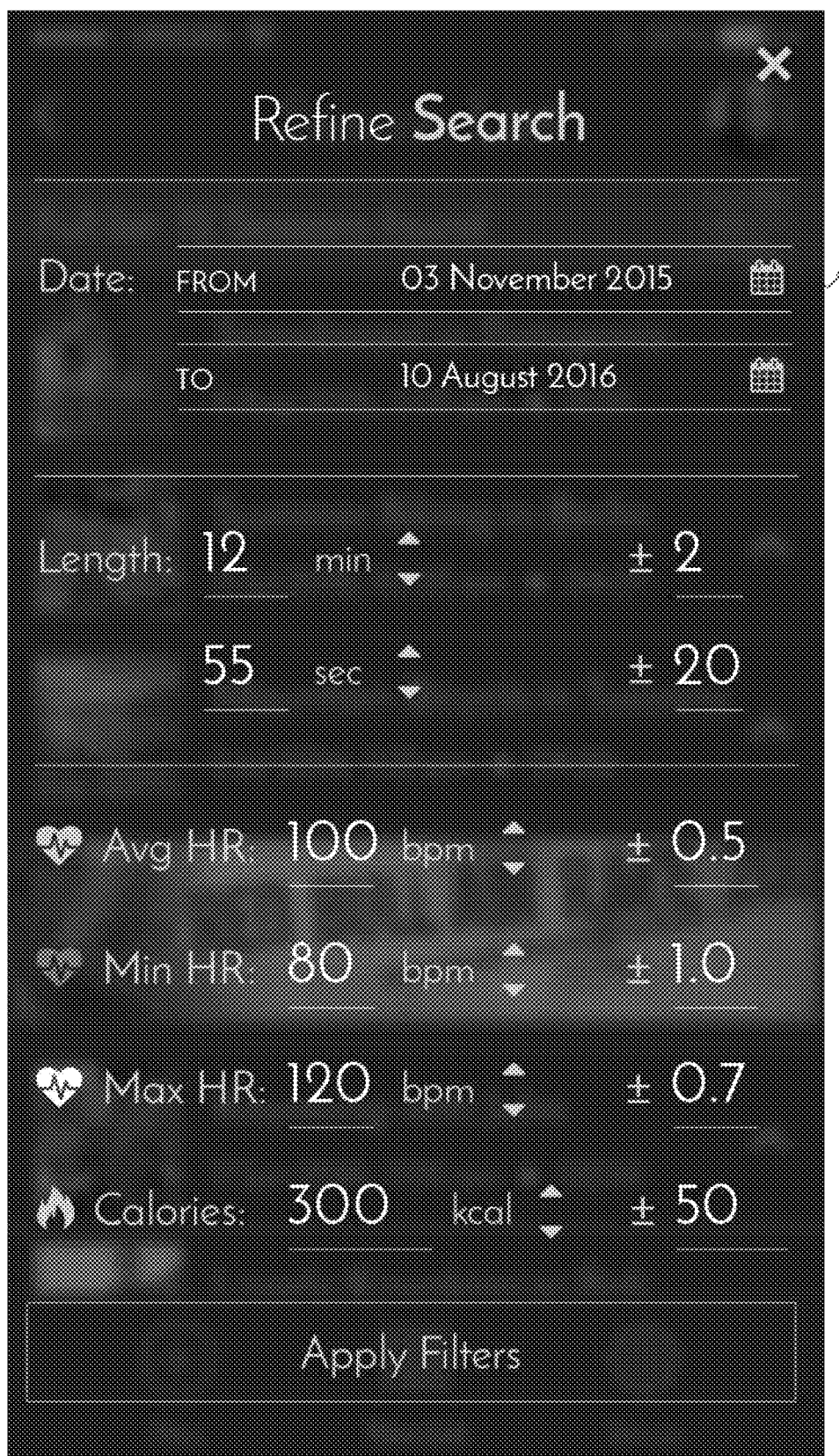
FIG. 28 depicts an exemplary "session search" screen shot for the application depicted in FIG. 15, allowing a user to search for sessions that meet certain criteria.
Figure 29:
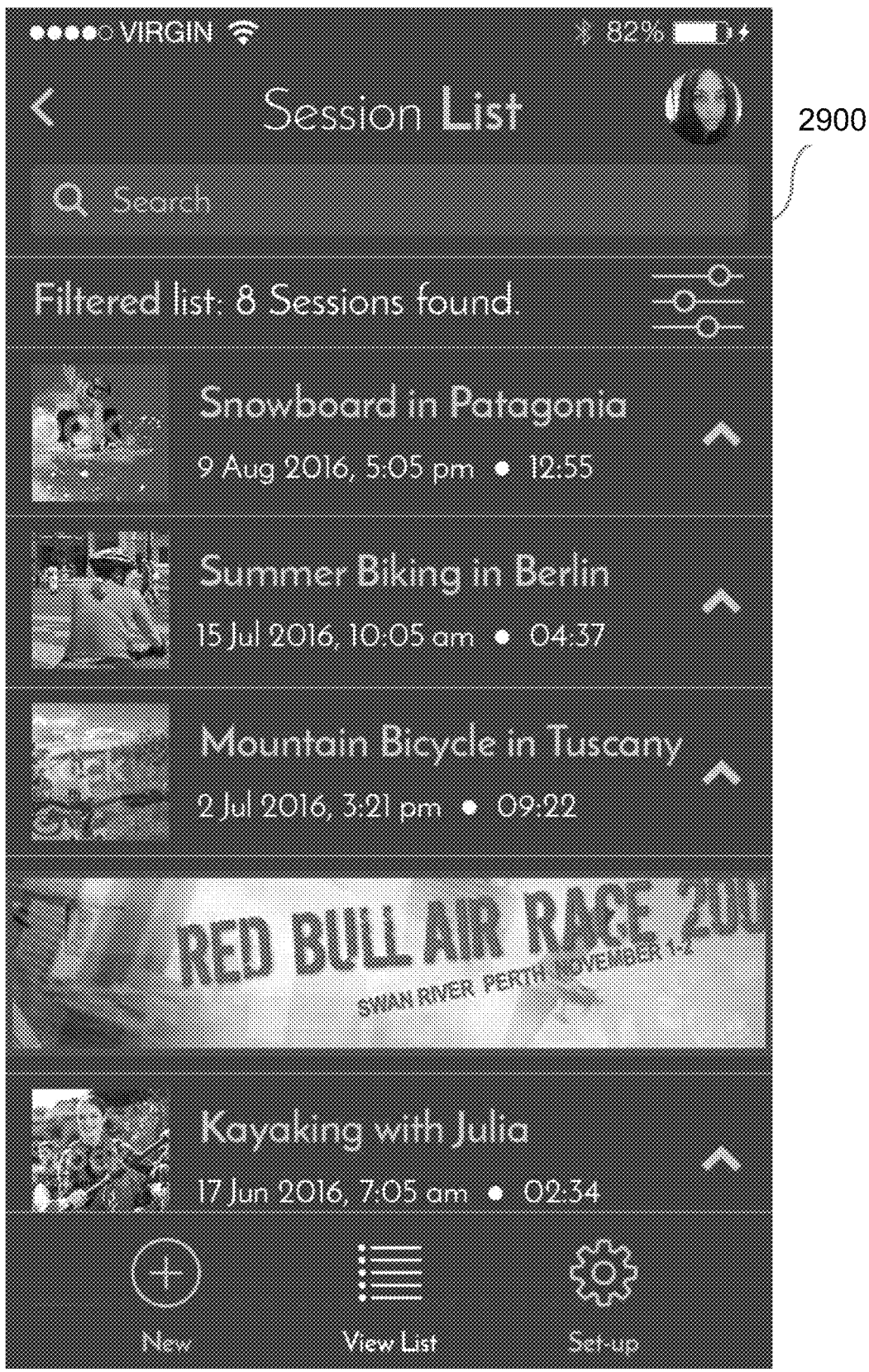
FIG. 29 depicts an exemplary "list" screen shot for the application depicted in FIG. 15, showing a result for the criteria shown in FIG. 28.

Not only can data within a session be searched, but so too can data from multiple sessions. For example, FIG. 28 shows an exemplary "session search" screen 2800, where a user can enter particular search criteria, including session date, session length, biometric events, video event, self-realization event, etc. FIG. 29 shows an exemplary "list" screen 2900, showing sessions that meet the entered criteria.

The foregoing description of a system and method for using, processing, and displaying biometric data, or a resultant thereof, has been presented for the purposes of illustration and description. It is not intended to be exhaustive or to limit the invention to the precise forms disclosed, and many modifications and variations are possible in light of the above teachings. Those skilled in the art will appreciate that there are a number of ways to implement the foregoing features, and that the present invention it not limited to any particular way of implementing these features. The invention is solely defined by the following claims.

What is claimed is:

1. A system for detecting COVID-19 in a user, comprising:
    at least one server in communication with a wide area network (WAN); and
    at least one memory device for storing machine readable instructions, at least a first set of said machine readable instructions being provided to a mobile computing device via said at least one server and said WAN, said first set of said machine readable instructions being adapted to operate on said mobile computing device and perform the steps of:
        receiving pulse and oxygen saturation level data from a pulse oximeter attached to said user periodically over a period of time, resulting in a plurality of sets of said pulse oximeter data;
        receiving movement data during said period of time, said movement data being indicative of at least movement of said user with respect to at least one fixed location; and
        identifying at least one of said plurality of sets of pulse oximeter data as being accurate when said movement data indicates that said movement of said user with respect to said fixed location is equal to or less than a pre-determined amount;
    wherein a second set of said machine readable instructions are adapted to perform the steps of:
        storing at least said accurate set of pulse oximeter data on said user and comparing it to previously stored pulse oximeter data from said user to determine a differential;
        comparing said differential to at least one known value; and
        using at least said comparison to help determine whether said user is currently suffering from COVID-19.

2. The system of claim 1, wherein said movement data is generated using at least an accelerometer within said mobile computing device.

3. The system of claim 2, wherein said movement data is further indicative of at least movement of said mobile computing device with respect to said fixed location.

4. The system of claim 3, wherein said movement data is further generated using at least a touchscreen of said mobile computing device.

5. The system of claim 4, wherein said movement data is further indicative of at least movement of at least a portion of said user's hand with respect to said touch screen, said pulse oximeter being attached to a finger on said user's hand.

6. The system of claim 5, wherein said first set of machine readable instructions are further configured to perform the step of instructing said user to place their hand on a particular portion of said touch screen, thereby allowing said computing device to determine whether said portion of said user's hand is moving during said period of time.

7. The system of claim 1, wherein said first set of machine readable instructions are further configured to acquire temperature data of said user during said period of time, said temperature data being used in helping to determine whether said user is suffering from COVID-19.

8. The system of claim 1, wherein said first set of machine readable instructions are further configured to acquire respiratory rate data of said user during said period of time, said respiratory rate data being used in helping to determine whether said user is suffering from COVID-19.

9. The system of claim 1, wherein said second set of machine readable instructions are further configured to use said comparison to determine a likelihood that said user is suffering from COVID-19, wherein said likelihood is determined using artificial intelligence (AI).

10. The system of claim 1, wherein said second set of said machine readable instructions are provided to said mobile computing device via said at least one server and said WAN, allowing artificial intelligence (AI) to determine whether said user is currently suffering from COVID-19.

11. The method of claim 1, further comprising the step of said mobile computing device acquiring respiratory rate data of said user during said period of time, said respiratory rate data being used in helping to determine whether said user is suffering from coronavirus.

12. The method of claim 11, wherein said movement data is further used to determine said user's respiratory rate.

13. A method for using at least a mobile computing device to detect coronavirus in a user, comprising the steps of:
    receiving by said mobile computing device pulse and oxygen saturation level data from a pulse oximeter attached to said user periodically over a period of time, resulting in a plurality of sets of said pulse oximeter data;
    receiving movement data during said period of time, said movement data being indicative of at least movement of said user with respect to at least one fixed location;
    identifying at least one of said plurality of sets of pulse oximeter data as being accurate when said movement data indicates that said movement of said user with respect to said fixed location is equal to or less than a pre-determined amount;
    storing at least said accurate set of pulse oximeter data on said user and comparing it to previously stored pulse oximeter data from said user to determine a differential;

comparing said differential to at least one known value; and using at least said comparison to determine whether said user is suffering from coronavirus.

14. The method of claim 13, wherein said movement data is generated using at least an accelerometer within said mobile computing device.

15. The method of claim 14, wherein said movement data is further indicative of at least movement of said mobile computing device with respect to said fixed location.

16. The method of claim 15, wherein said movement data is further generated using at least a touchscreen of said mobile computing device.

17. The method of claim 16, wherein said movement data is further indicative of at least movement of at least a portion of said users hand with respect to said touch screen, said pulse oximeter being attached to a finger on said users hand.

* * * * *